US008889662B2

(12) United States Patent
Navara

(10) Patent No.: US 8,889,662 B2
(45) Date of Patent: Nov. 18, 2014

(54) METHOD TO ALTER SEX RATIOS IN AVIAN OFFSPRING

(75) Inventor: Kristen J. Navara, Athens, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 357 days.

(21) Appl. No.: 13/201,505

(22) PCT Filed: Mar. 1, 2010

(86) PCT No.: PCT/US2010/025722
§ 371 (c)(1),
(2), (4) Date: Sep. 2, 2011

(87) PCT Pub. No.: WO2010/101802
PCT Pub. Date: Sep. 10, 2010

(65) Prior Publication Data
US 2012/0046263 A1 Feb. 23, 2012

Related U.S. Application Data

(60) Provisional application No. 61/156,575, filed on Mar. 2, 2009.

(51) Int. Cl.
A61K 31/56 (2006.01)
A01K 67/02 (2006.01)
A01K 45/00 (2006.01)

(52) U.S. Cl.
CPC ............... A01K 67/02 (2013.01); A01K 45/00 (2013.01)
USPC ........................................................ 514/182

(58) Field of Classification Search
USPC ........................................................ 514/182
See application file for complete search history.

(56) References Cited

U.S. PATENT DOCUMENTS 5,575,237 A 11/1996 Ferguson
2005/0143465 A1 6/2005 Pageat

FOREIGN PATENT DOCUMENTS

WO 2010/101802 9/2010

OTHER PUBLICATIONS

Pike et al., Proc. R. Soc. B, 2006;273:1093-1098.*
Correa et al., Biol. Lett., 2005;1:215-219.*
Alonso-Alvarez, et al., "Female body condition and brood sex ratio in Yellow-legged Gulls *Larus cachinnans*," 2003, *Ibis*; 145:220-226.
Alonso-Alvarez. "Manipulation of the primary sex-ratio: an updated review." 2006. *Avian and Poultry Biology Reviews*. 17:1-20.
Arnold et al. "Primary sex ratios in birds: problems with molecular sex identification of undeveloped eggs". 2003. *Molecular Ecology*. 12:3451-3458.
Ashwell et al., "Hormonal regulation of leptin expression in broiler chickens," 1999, *American Journal of Physiology*; 276:226-232.

(Continued)

Primary Examiner — San-Ming Hui
(74) Attorney, Agent, or Firm — Mueting, Raasch & Gebhardt, P.A.

(57) ABSTRACT

The present invention includes methods of influencing the sex chromosome ovulated by a female bird and altering the sex ratio in avian offspring by altering the exposure of an ovulating female bird to one or more stress hormones. In some aspects, the method includes exposing an avian female to a glucocorticoid, such as for example, corticosterone, after the completion of rapid yolk deposition and prior to ovulation.

20 Claims, 10 Drawing Sheets

(56) References Cited

OTHER PUBLICATIONS

Ellegren et al. "Sex ratio adjustment in relation to paternal attractiveness in a wild bird population". 1996. *PNAS*. 93:11723-11728.

Gam et al., "Effects of progesterone and corticosterone administration on offspring primary sex ratio in the zebra finch (*Taeniopygia guttata*)," 2009 Annual Meeting of the Society for Integrative and Comparative Biology, Jan. 3-7, 2009, Boston, Massachusetts. Meeting Abstract P3.149. Presented Tuesday Jan. 6, 2009. 3 pages total.

Goerlich et al. "Testosterone has a long-term effect on primary sex ratio of first eggs in pigeons-in search of a mechanism." 2009. *Gen Comp Endocrinol*. 163:184-192.

Kilner et al. "Primary and secondary sex ratio manipulation by zebra finches". 1998. *Animal Behavior*. 56:155-164.

Komdeur et al. 2002. "Pre-ovulation control of hatchling sex ratio in the *Seychelles warbler*". Proceedings of the Royal Society of London Series B-Biological Sciences. 269:1067-1072.

Kwok et al., "Cloning of Chicken Glucocorticoid Receptor (GR) and Characterization of its Expression in Pituitary and Extrapituitary Tissues," 2007, *Poult Sci*; 86:423-430.

Navara et al., "Variable Effects of Yolk Androgens on Growth, Survival, and Immunity in Eastern Bluebird Nestlings," 2005, *Physiological and Biochemical Zoology*; 78(4):570-578.

Navara et al., "Yolk Testosterone Stimulates Growth and Immunity in House Finch Chicks," 2006, *Physiological and Biochemical Zoology*; 79(3):550-555.

Navara et al., "Yolk Antioxidants Vary with Male Attractiveness and Female Condition in the House Finch (*Carpodacus mexicanus*)," 2006, *Physiological and Biochemical Zoology*; 79(6):1098-1105.

Navara et al., "Yolk androgens vary inversely to maternal androgens in Eastern Bluebirds: an experimental study," 2006, *Functional Ecology*; 20:449-456.

Navara et al., "Yolk andorgens as pleiotropic mediators of physiological processes: A mechanistic review," 2008, *Comparative Biochemistry and Physiology, Part A*. 9 pages.

Navara et al., "Yolk androgen deposition as a compensatory strategy," 2006, *Behav Ecol Sociobiol*; 60:392-398.

Okekpe et al., "Effect of diet on periovulatory levels of steroid hormones and primary sex ration in zebra finches," 2009 Annual Meeting of the Society for Integrative and Comparative Biology, Jan. 3-7, 2009, Boston, Massachusetts. Meeting Abstract P2.167. Monday, Jan. 5, 2009. 3 pages total.

Pike et al., "Offspring sex ratio is related to paternal train elaboration and yolk corticosterone in pea fowl," 2005, *Biology Letters*; 1:204-207.

Pinson et al. "Acute corticosterone administration during meiotic segregation stimulates females to produce more male offspring". 2011. *Physiol. Biochem. Zool*. 84(3):292-298.

Rutkowska et al. "Maternal testosterone affects the primary sex ratio and offspring survival in zebra finches". 2006. *Animal Behaviour*. 71:1283-1288.

Rutkowska et al. "Meiotic drive and sex determination: molecular and cytological mechanisms of sex ratio adjustment in birds" 2008. Philosophical Transactions of the Royal Society B-Biological Sciences. 363:1675-1686.

Schwabl, "Yolk is a source of maternal testosterone for developing birds," 1993, *Proceedings of the National Academy of Sciences of the USA*; 90:11446-11450.

Velando, "Experimental manipulation of maternal effort produces differential effects in sons and daughters: implications for adaptive sex ratios in the blue-footed booby," 2002, *Behavioral Ecology*; 13:443-449.

Wild et al., "A sex allocation theory for vertebraes: combining local resource competition and condition-dependent allocation," 2007, *American Naturalist*; 170:E112-E128.

Young et al. "Evolution of sex-biased maternal effects in birds: I. Sex-specific resource allocation among simultaneously growing oocytes". 2004. *Journal of Evolutionary Biology*. 17:1355-1366.

International Preliminary Report on Patentability and Written Opinion in PCT/US2010/025722, issued on Nov. 5, 2010. 8 pages.

International Search Report in PCT/US2010/025722, issued on Nov. 5, 2010. 4 pages.

\* cited by examiner

METHOD TO ALTER SEX RATIOS IN AVIAN OFFSPRING

CONTINUING APPLICATION DATA

This application is the §371 U.S. National Stage of International Application No. PCT/US2010/025722, filed 1 Mar. 2010, which claims the benefit of U.S. Provisional Application Ser. No. 61/156,575, filed Mar. 2, 2009, each of which are incorporated by reference herein.

BACKGROUND

In the poultry layer and broiler industries, approximately 50% of all chicks that hatch are killed immediately after hatching, because they are the non-preferred sex. Methods for the manipulation of hens such that they preferentially produce more female or male offspring has the potential to increase efficacy and productivity in the poultry industry. Thus, there is a need for improved methods of altering sex ratios in avian offspring.

SUMMARY OF THE INVENTION

The present invention includes a method of altering the sex ratio in avian offspring, the method including providing an adrenal glucocorticosteroid to an ovulating avian female.

In another aspect, the present invention includes a method of influencing the sex chromosome ovulated by a female bird, the method including providing an adrenal glucocorticosteroid to the ovulating female bird.

In some embodiments of the methods of the present invention, the adrenal glucocorticosteroid comprises a corticosterone. In some embodiments of the methods, the glucocorticosteroid is provided before the completion of meiosis I in an oocyte. In some embodiments of the methods, the glucocorticosteroid is provided at the time of sex chromosome segregation in an oocyte. In some embodiments of the methods, the glucocorticosteroid is provided after the completion of rapid yolk deposition and prior to ovulation.

In some embodiments of the methods of the present invention, the adrenal glucocorticosteroid is administered to the ovulating avian female. In some embodiments of the methods, the adrenal glucocorticosteroid is provided by exposing the ovulating avian female to a stress.

In some embodiments of the methods of the present invention, the resultant sex ratio in the avian offspring is more than 50% male offspring. In some embodiments, the probability of a male embryo is greater than 50%.

The present invention also includes a method of influencing the sex chromosome ovulated by a female bird or altering the sex ratio in avian offspring, the method including altering the exposure of an ovulating female bird to one or more stress hormones. In some embodiments, altering the exposure of the ovulating female bird to one or more stress hormones includes the administration of an inhibitor of a stress hormone. In some embodiments, the inhibitor of a stress hormone is administered before the completion of meiosis I in an oocyte, at the time of sex chromosome segregation in an oocyte, or provided after the completion of rapid yolk deposition and prior to ovulation. In some embodiments, the resultant sex ratio in the avian offspring is more than 50% male offspring. In some embodiments, the resultant sex ratio in the avian offspring is more than 50% female offspring.

In some embodiments of the methods of the present invention, the avian is a chicken. In some embodiments, the chicken is a broiler or a layer.

In some embodiments of the methods of the present invention, the avian is a passerine or an exotic. In some embodiments, the exotic is a zebra finch.

All headings are for the convenience of the reader and should not be used to limit the meaning of the text that follows the heading, unless so specified.

The terms "comprises" and variations thereof do not have a limiting meaning where these terms appear in the description and claims.

Unless otherwise specified, "a," "an," "the," and "at least one" are used interchangeably and mean one or more than one.

BRIEF DESCRIPTION OF THE FIGURES

FIG. 7C shows log plasma corticosterone concentrations (mean+standard error) of hens in the UN, CONT, and CORT treatment groups at 1 hour (n=12, 5, 6) and 4 hour (n=12, 7, 6). Hormone concentrations were not compared among time points. Different letters or an asterisk above the bars denote statistical differences.

DETAILED DESCRIPTION OF ILLUSTRATIVE EMBODIMENTS OF THE PRESENT INVENTION

Figure 1:
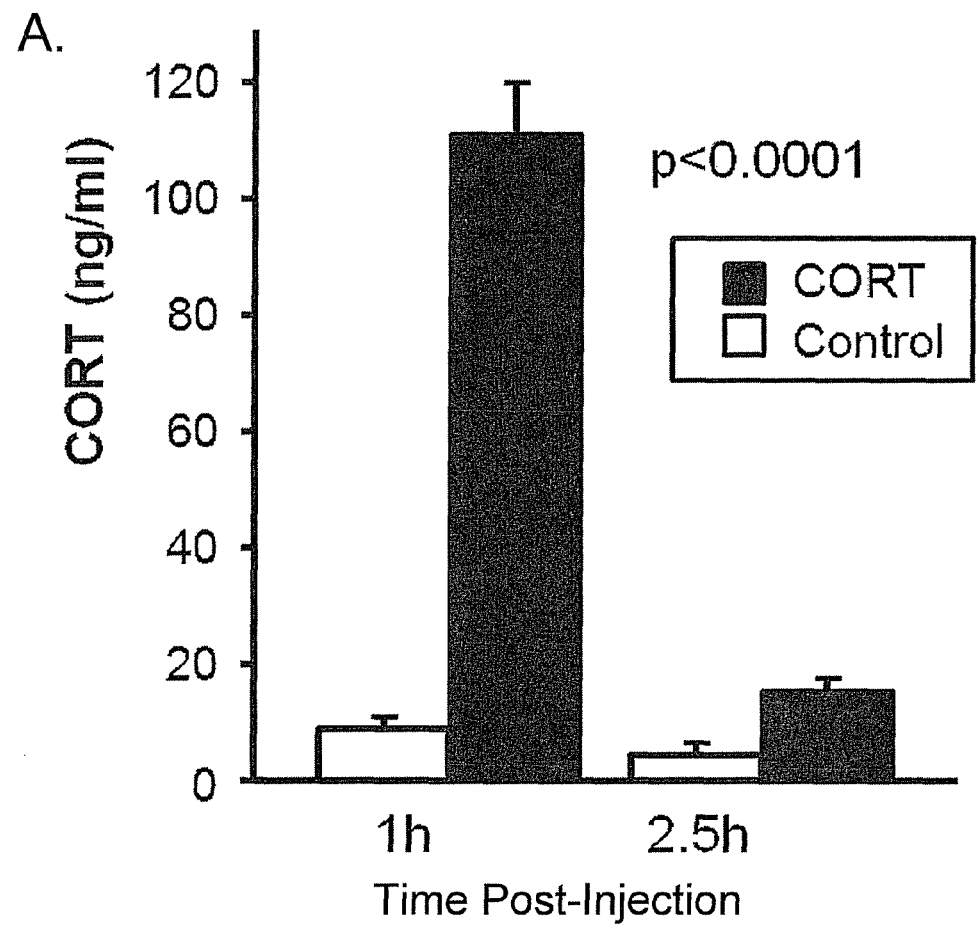
FIG. 1 presents plasma corticosterone concentrations (ng/ml) of control and corticosterone-injected female zebra finches (FIG. 1A) and primary sex ratio (percentage of male embryos) in offspring of corticosterone-injected and control zebra finch females (FIG. 1B).

From a commercial standpoint, particularly in the poultry industry, the ability to influence offspring sex would be very useful technology. Currently, 50% of offspring hatched in both the layer and the broiler industries are discarded, because only females are useful in the layer industry and only males are useful in the broiler industry. The ability to control offspring sex would save millions of dollars and would also save millions of animal lives. Current techniques of reducing costs associated with the production of "unwanted sexes" require the industry workers to wait until after hatch when the offspring can be surgically or genetically sexed and the unwanted offspring discarded. The ability to control the offspring sex prior to hatching would not only save on incubator space required for incubating the 50% extra egg quantities, but would also decrease the manpower for hen insemination, egg collection, the costs of vaccinating the eggs that would eventually produce "unwanted" offspring, and would increase the lifetime productivity of hens.

The present invention demonstrates for the first time that altering the exposure of a female bird to one or more stress response hormones at about the time of meiotic segregation in the oocyte influences the sex chromosome ovulated by the female bird and results in an alteration of the sex ratio of the offspring. In some embodiments, the present invention demonstrates that providing a female bird with an exposure to a stress response hormone at about the time of meiotic segregation in the oocyte results in an altering (also referred to herein as an alteration, skewing, or manipulation) of the sex ratio of the offspring. With the present invention, an altered sex ratio includes a resultant sex ratio in the avian offspring such that more than 50% of the offspring are of a given sex, for example, more than 50% male offspring or more than 50% female offspring. In a preferred embodiment, more than 50% of the offspring are male. With the present invention, an altered sex ratio includes a probability of greater than 50% that an embryo is of a given sex, for example, a probability of greater than 50% that an embryo is a male embryo or a probability of greater than 50% that an embryo is a female embryo. In a preferred embodiment, the probability is greater than 50% that an embryo is a male embryo.

In the avian system, the female is heterogametic, and is therefore responsible for determining the sex of offspring. In the avian ovary, thousands of ovarian follicles, each containing both a W and a Z sex chromosome, develop very slowly until they either undergo cell death or are recruited into the ovulatory hierarchy destined for ovulation. At this point, the follicles grow very quickly, and can be categorized according to size (F1 to F5, with F1 as the largest and F5 as the smallest). This process of rapid yolk deposition (RYD) begins 6-11 days before ovulation, during which concentric rings of yolk are deposited, and stops approximately twenty-four hours prior to ovulation. The amount of yolk deposited into each layer depends upon the amount of lipid-based yolk precursors available in the bloodstream for deposition. During a majority of time in the avian ovary, the follicles are arrested partway through meiosis I, remaining in the diploid state and retaining both sex chromosomes. At a point prior to ovulation, meiosis I completes, segregating the sex chromosomes such that one is retained in the developing oocyte that can potentially produce the offspring, and one is expelled into a small polar body with no further developmental capacity. After this point, the oocyte is ovulated into the infundibulum, leaving behind its supportive follicular layers, and traveling through the reproductive tract. Follicles within a clutch are ovulated and laid within about 24 h of one another. Thus, the sex of the offspring is set at the time of the first meiotic division when one sex chromosome is allocated to the oocyte and the other to the polar body, several hours prior to ovulation.

With the present invention, an ovulating female may be provided with a stress hormone, such as for example, an adrenal glucocorticosteroid, a sex hormone, such as, for example, progesterone, estrogen, or testosterone, or an inhibitor thereof, prior to ovulation. An adrenal glucocorticosteroid includes, but is not limited to, corticosterone, cortisol, cortisone, and combinations thereof. In a preferred embodiment, the adrenal glucocorticosteroid is corticosterone (also referred to herein as "CORT"). In birds, corticosterone is the primary glucocorticoid. It actively regulates energy balance and utilization during stressful events and balances physiological activities to maximize the chances of survival. Because the left adrenal gland is within close proximity to the ovary in the bird, glucocorticoids may mediate ovarian activities as well. In fact, circulating CORT rises in females before and is necessary for successful ovulation in birds. In addition, the egg yolk, which directly contacts the germinal disc containing the sex chromosomes, accumulates CORT during rapid yolk deposition, providing another potential mechanism of CORT exposure during follicular maturation and meiosis. Thus, CORT could potentially act to regulate the rate of follicular growth and/or segregation of avian sex chromosomes as well. Indeed, several avian studies show that chronic elevation of maternal CORT significantly skews primary offspring sex ratios. In each case, birds with chronically high CORT levels produced significantly more females.

With the present invention, a stress hormone or inhibitor thereof may be administered in a short term, limited time frame ("acute") or provided over a longer term time frame ("chronic"). In a preferred embodiment, acute delivery of a stress hormone or inhibitor thereof is utilized. A stress hormone or inhibitor thereof may be provided by any of a wide variety of means.

In some embodiments, the stress hormone or inhibitor thereof is provided exogenously, by the administration of a composition including an amount of a stress hormone or inhibitor thereof to the female bird. For example, a glucocorticosteroid may be administered by routes including, but not limited to, injection, topical, and oral. Injection includes, but is not limited to intraperitoneal injection (ip), intravenous injection (iv), intramuscular injection (im), and subcutaneous injection (sc). A glucocorticosteroid may be administered by a pump, such as, for example, an osmotic pump.

A stress hormone or inhibitor thereof may be formulated for administration according to any of the wide variety of formulations known in the pharmacological arts. In some embodiments, a composition may further include water, oil, or other pharmaceutically acceptable carrier. In some embodiments, a composition may be formulated for injection, including, for example, intraperitoneal injection, intravenous injection, intramuscular injection, and/or subcutaneous injection. In some embodiments, a composition may be formulated for topical or mucosal administration. In some embodiments, a composition may be formulated for intranasal, intraocular, or oral administration. In some embodiments, a composition may be formulated for spraying or aerolizing. Such compositions may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate and gentamicin. Diluents, include, but are not limited to, water aqueous buffer (such as buffered saline), alcohols, and polyols (such as glycerol).

A stress hormone or inhibitor thereof may be administered at any of a variety of dosages. A stress hormone or inhibitor thereof may be administered at a physiological dose. A stress hormone or inhibitor thereof may be administered at a dose that is higher or lower than physiological, for example at a dosage that is about two-fold, about five-fold, about ten-fold, about twenty-five-fold, about fifty-fold, about one hundred-fold, about five hundred-fold, or about one thousand-fold higher or lower than physiological. A stress hormone or inhibitor thereof may be administered at a range of any two of the dosages set forth above. For example, a stress hormone or inhibitor thereof may be administered at a dosage of about two-fold to about a thousand-fold higher; about two-fold to about a thousand-fold lower; about ten-fold to about a hundred fold higher; about ten-fold to about a hundred-fold lower; about ten-fold higher to about ten-fold lower; about a hundred-fold higher to about a hundred-fold lower; and about a thousand-fold higher to about a thousand-fold lower of physiological. A stress hormone or inhibitor may be administered at any of the dosages described in the Examples and Figures included herewith.

In some embodiments of the methods of the present invention, a stress hormone is provided endogenously, by subjecting the bird to one or more environmental or social conditions that induce a stress response in the bird, leading to a short-term elevation in one or more circulating glucocorticosteroids. Such a stress response may be induced, for example, by handling, including, but not limited to, delivery of a placebo injection, length of day light, light conditions, noise, food availability, and/or crowding.

In some embodiments of the present invention, the exposure of a female bird to one or more stress response hormones is altered by the administration of one or more inhibitors of a stress response hormone. The exposure to such an inhibitor may alter a sex ratio so that the resultant sex ratio in the avian offspring is more than 50% male offspring or more than 50% female offspring. Such inhibitors include, but are not limited to, a glucocorticoid receptor (GR) antagonist, such as, for example, RU-486 or cyproterone, a glucocorticoid receptor agonist, such as for example, fludrocortisone and dexamethasone, a mineralocorticoid receptor (MR) antagonist, a mineralocorticoid receptor agonist, and other synthetic steroid compounds.

With the present invention, a stress hormone or an inhibitor thereof may be provided at about the midsequence of ovulation; after the completion of rapid yolk deposition; prior to ovulation; before the completion of meiosis I in an oocyte; before the extrusion of a polar body, just prior to the onset of sex chromosome segregation in an oocyte; at about the time of sex chromosome segregation in an oocyte; and/or at about the time of meiotic segregation in an oocyte. A stress hormone or inhibitor thereof may be provided in an interval set by any two of the above recited time points. For example, a stress hormone or an inhibitor thereof may be provided after the completion of rapid yolk deposition and prior to ovulation. A stress hormone or an inhibitor thereof may be provided after the completion of rapid yolk deposition and before the completion of meiosis I in an oocyte. A stress hormone or inhibitor thereof may be provided at about one hour, about two hours, about three hours, about four hours, about five hours, or about six hours prior to ovulation. A stress hormone or inhibitor thereof may be provided at an interval of any two of the above described time points; for example, at about one to about two hours, at about one to about six hours, at about two to about four, about four to about six hours prior to ovulation, and about five to about six hours. A stress hormone or inhibitor may be provided at any of the time points set forth in the Examples and Figures included herewith.

The methods of the present invention may be administered to any of a variety of avian species, including, but not limited to, poultry, passerines, and exotic bird species. As used herein, poultry includes domesticated birds that are kept for the purpose of collecting their eggs, or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants. As used herein, a passerine is a bird of the order Passeriformes, which includes more than half of all bird species, and are sometimes referred to perching birds or songbirds. Exotics can include, for example, any of a variety of parrots, parakeets, canaries, cockatiels, macaws, and finches. Examples of finches can include, for example, gouldian finches, red-headed parrot finch, society finches, spice finches, strawberry finches, and zebra finches.

The present invention includes kits that provide for the administration of a stress hormone or inhibitor thereof, such as, for example, a corticosteroid, to a bird in order to alter the sex ratio of the offspring. Such kits may provide an amount of a stress hormone and/or inhibitor. Kits of the present invention may include other reagents such as buffers and solutions needed to practice the invention are also included. Portions of such kits of the present invention may be included in packaging material. As used herein, the phrase "packaging material" refers to one or more physical structures used to house the contents of the kit. The packaging material is constructed by well known methods, preferably to provide a sterile, contaminant-free environment. As used herein, the term "package" refers to a solid matrix or material such as glass, plastic, paper, foil, and the like, capable of holding within fixed limits a stress hormone. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

A Treatment to Alter Sex Ratios if Offspring in Birds

Previous work suggests that females may have control over which sex chromosome is retained in the oocyte and which is expelled into the polar body, resulting in an ability to skew offspring sex ratios (Correa et al., 2005, *Biology Letters;* 1:215-8; Love et al., 2008, *Hormones and Behavior;* 53:104-11). Three natural hormones have been implicated as key players in this process: the reproductive hormones, testosterone and progesterone, and the stress hormone, corticosterone. Because progesterone and testosterone are tightly linked to ovulatory processes, treatment of female birds with these hormones tends to disrupt ovulation and egg-laying. This example tests the effects of an acute treatment of corticosterone on the resulting sex of a mid-sequence oocyte and thus a mid-sequence embryo.

Glucocorticoids are potent mediators of physiological processes that are released in response to physiologically and or psychologically stressful events. In birds, corticosterone (CORT) is the primary glucocorticoid; it actively regulates energy balance and utilization during stressful events and balances physiological activities to maximize the chances of survival. Because the left adrenal gland is embedded in the ovary in the bird, glucocorticoids can mediate ovarian activities as well. In fact, circulating CORT rises in females before and is necessary for successful ovulation in birds. Recent studies in four avian species show that females with high corticosterone (CORT) concentrations skew offspring sex ratios significantly towards females (Pike and Petrie, 2005, *Biology Letters;* 1:204-7; Pike and Petrie, 2006, *Proceedings of the Royal Society of London, Series B;* 273:1093-8; Bonier et al., 2007, *Behavioral Ecology;* 18:1045-50). In two of these cases, CORT concentrations were directly manipulated using long-term silastic implants that elevated CORT consistently for long periods of time. In these cases, sex ratios were skewed significantly towards females.

This example examined the effects of an acute elevation of CORT that coincided at the time of sex chromosome segregation in two avian species. The first species, the zebra finch (*Taeniopygia guttata*) was chosen because this species has a particular aptitude for skewing offspring sex ratios in response to natural stimuli such as food availability and mate attractiveness. The second species, the chicken, was used due to its commercial applicability already described above.

Effects of Maternal CORT Administration on Offspring Sex in Zebra Finches

This experiment was conducted to determine whether a single injection of CORT at the critical time of sex chromosome segregation is sufficient to skew offspring sex ratios towards females. Female zebra finches were monitored for signs of nest-building and egg-laying. Approximately 19 h following the appearance of the first egg (1 h before sex chromosome segregation), females received one of two treatments: (1) a high dose of CORT (20 ug in 50 ul peanut oil), or (2) a control treatment (50 ul peanut oil). Because oviposition and ovulation are nearly concurrent, ovulation of the second egg took place when the first egg was laid. Thus, the egg that would be affected by our treatment was the third egg in the sequence. Eggs were labeled as they were laid and were collected after 6 d of incubation for molecular sexing analysis as described above. The percentage of females producing male offspring in each group were calculated and compared using chi square analyses. Blood samples were taken from a subset of females 1 h and 2.5 h post injection to verify that the CORT injection did, in fact, elevate circulating maternal CORT concentrations. CORT was quantified using a standard radioimmunoassay and CORT concentrations were log transformed and analyzed using an analysis of variance (ANOVA).

An acute treatment with a high dose of corticosterone significantly increased circulating CORT concentrations in female zebra finches compared to controls within 1 h of injection ($p<0.0001$). CORT concentrations remained higher in the CORT treated females 2.5 h post-injection, but not significantly so ($p=0.08$). Thus, CORT concentrations were elevated at the onset of meiotic segregation (4 h prior to ovulation—1 h after injection) and likely throughout the entire segregation process (FIG. 1A). Embryos in eggs laid by females that had been injected with CORT were significantly more likely to be male compared to controls ($\chi 2=12.87$, $p<0.0001$). 71% of eggs produced by CORT injected females were male compared to 46% produced by control injected females (FIG. 1B).

Effects of Maternal CORT Administration on Offspring Sex in Chickens

This experiment was similar to the previous one in that a single injection of CORT was provided at the time of meiotic segregation and the sexes of the resulting eggs were quantified. Laying patterns of female white leghorn and brown hyline hens were monitored and timed. Females that were laying between 1000 and 1200 h EST were included in the experiment. Females were artificially inseminated using pooled semen from 5-10 roosters at two time points prior to treatment.

Approximately 19 h following the appearance of a mid-sequence egg, females received one of three treatments: (1) a high dose of CORT (2 mg in 0.5 ml peanut oil), (2) a control treatment (0.5 ml peanut oil), or (3) no injection treatment. The egg corresponding to the next ovulation event was labeled, collected, and incubated at 37° C. for a period of 7 days to allow for embryonic development. Embryos were separated and sexed using PCR based techniques as described above. The percentage of females producing male offspring in each group were calculated and compared using chi square analyses. Also, as described above, blood samples were taken from a subset of females one hour and four hours after injection to verify that the CORT treatment did, in fact, elevate maternal CORT concentrations at the time of meiotic segregation. CORT was quantified using a standard radioimmunoassay and CORT concentrations were log transformed and analyzed using an analysis of variance (ANOVA).

Figure 2:
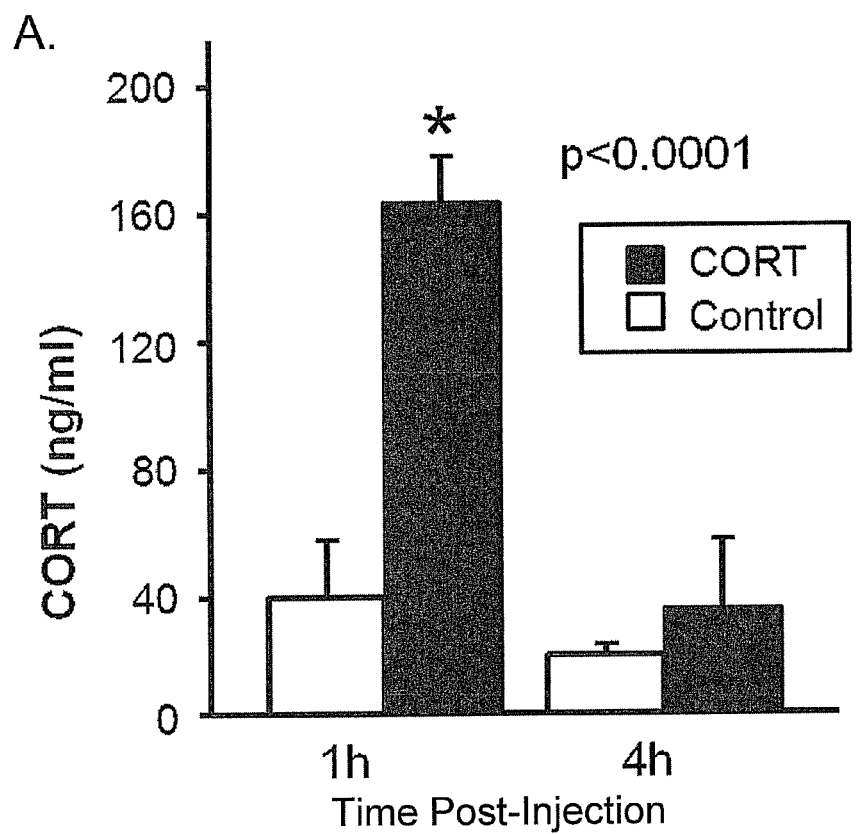
FIG. 2 presents plasma corticosterone concentrations (ng/ml) of control and corticosterone-injected female chickens (FIG. 2A) and primary sex ratio (percentage of male embryos) in offspring of corticosterone-injected, control-injected and non-manipulated female chickens (FIG. 2B).

As with the zebra finches, an acute treatment with a high dose of corticosterone significantly increased circulating CORT concentrations in hens compared to controls within one hour of injection ($p<0.0001$) (FIG. 2A). This difference disappeared by four hours post-injection, which is not surprising given that previous work done in chickens showed that injection with corticosterone results in elevated CORT concentrations for approximately 90 minutes following injection, similar to that seen with the zebra finches above. Thus, CORT concentrations were elevated at the onset of meiotic segregation and likely throughout the segregation process in chickens as well.

As with the zebra finches, embryos in eggs laid by female chickens that had been injected with CORT were significantly more likely to be male compared to controls ($\chi 2=10.15$, $p=0.002$) and compared to non-injected females ($2=35.86$, $p<0.0001$). In addition, control birds produced significantly more males compared to non-injected females ($\cdot 2=8.91$, $p<0.005$) (FIG. 2B).

Discussion

This example demonstrates that a single corticosterone treatment can be used in two avian species to influence the sex that results from a mid-sequence ovulation. The CORT treatments used here produced pharmacological concentrations of CORT in circulation. Future studies will focus on treatments that produce concentrations within the physiological range. However, the results of experiment 2 suggest that even the stress associated with the injection itself may have contributed to an increase in the number of males produced, as control-injected birds produced significantly more males compared to uninjected birds. More studies are needed to determine the doses of CORT necessary for skewing offspring sex ratio, as well as to determine whether a higher dose of CORT may produce an even higher percentage of male offspring.

The results documented here were contrary to predictions given that long-term treatment with CORT using silastic implants skewed offspring sex ratios towards females, indicating that acute and chronic CORT might act on offspring sex determination through different mechanisms. Further studies will determine the best time-frame in which to perform injections in relation to the processes of meiotic segregation and ovulation, and to determine an easy treatment method which could be easily used by the industry worker.

Example 2

Corticosterone Treatment During Meiosis I Biases Offspring Sex Ratios Towards Males in Zebra Finches Researchers have documented significant skews in the primary sex ratios of avian offspring in relation to a variety of environmental and social cues. Zebra finches, in particular, adjust offspring sex ratio according to both the quality and quantity of available food, as well as male attractiveness. The mechanisms behind such manipulation of offspring sex remain elusive. Recent studies suggest that females with chronically elevated corticosterone levels (both naturally and artificially) produce significantly female biased offspring sex ratios. This example tested the effects of a pharmacological dose of corticosterone and progesterone given at the time of sex chromosome segregation on the primary sex ratio of zebra finch offspring to determine whether corticosterone acts on offspring sex at this critical period. Females were injected with 20 µg of corticosterone, 20 µg of progesterone or with a control oil vehicle control five hours prior to the predicted time of the $3^{rd}$ or $4^{th}$ ovulating follicle. The corticosterone treated group produced 72% males while the control injected group produced 61.9% males and the uninjected control group produced 37.5% in the 3rd or 4th ovulation of the sequence. Progesterone injections disrupted ovulation and oviposition in 90% of females. Corticosterone administration did not adversely affect oviposition or ovulation. Females injected with corticosterone had significantly elevated levels of corticosterone 20 minutes, 1 hour, and 2.5 hours post-injection and produced significantly more males compared to untreated females. The results of this example show that offspring sex ratios may be influenced at the time of meiotic division by acute exposure to corticosterone and provides evidence for the timing of this effect.

Significant skews in the primary sex ratios of avian offspring have been documented in relation to a variety of environmental and social cues, in a range of avian species (Burley, 1986, *Evolution;* 40:1191-1206; Burley et al., 1989, *Emu* 89:83-92; Ellegren et al., 1996, *PNAS;* 93:11723-11728; Okekpe, 2009, "Evidence that maternal diet alters steroid levels and primary sex ratio in the zebra finch. Dissertation," Auburn University; Pike and Petrie, 2005, *Animal Behavior;* 70:745-751; Pike and Petrie, 2005, *Biology Letters* 1:204-207; and Svensson and Nilsson, 1996, *Proceedings of the Royal Society of London Series B-Biological Sciences;* 263:357-361). Adaptive theories of sex allocation stipulate that deviations from the expected 50:50 offspring sex ratio will be influenced by environmental and social factors experienced during reproduction; females will adjust offspring sex ratio in accordance with environment conditions in order to maximize offspring survival and reproductive success (Lambin, 1994, *Ecology;* 75:224-235; Trivers and Willard, 1973, *Science;* 179:90-92; Wild and West, 2007, *American Naturalist;* 170:E112; and Wright et al., 1995, *American Naturalist;* 145:133-145). While many studies have shown that females adjust sex ratios postnatally by varying resource allocation, protection, and other behavioral variables, there is also evidence that females can negate the costly losses associated with sex-specific postnatal mortality by adjusting sex ratios in a primary manner, before fertilization (Kilner, 1998, *Animal Behavior;* 56:155-164; Komdeur et al., 2002, *Proceedings of the Royal Society of London Series B-Biological Sciences;* 269:1067-1072; reviewed in Rutkowska and Badyaev, 2008, *Philosophical Transactions of the Royal Society B-Biological Sciences;* 363:1675-1686). The physiological mechanisms underlying biases in primary avian sex ratio however, remain unclear.

Circulating hormones respond rapidly to environmental and social cues, follow annual and diurnal cycles and are important in reproductive physiology, thus it is likely that one or more hormones act as signal mediators between the environment and the physiological responses that control primary sex manipulation. Three hormones have been implicated as mediators of the sex determination process in birds, including testosterone (Goerlich et al., 2009, *Gen Comp Endocrinol;* 163:184-192; Rutkowska and Cichon, 2006, *Animal Behavior;* 71:1283-1288; Veiga et al., 2004, *Horm Behav;* 46:47-53) corticosterone (Bonier et al., 2007, *Behavioral Ecology;* 18:1045-1050; Pike and Petrie, 2005, *Animal Behavior;* 70:745-751; Pike and Petrie, 2005, *Biology Letters* 1:204-207; Pike and Petrie, 2006, *Proceedings of the Royal Society B-Biological Sciences;* 273:1093-1098), and progesterone (Correa et al., 2005, *Biology Letters;* 1:215-218). Because of its local abundance at the ovulatory site and its daily peak around the time of meiotic segregation (Etches and Cunningham, 1976, *British Poultry Science;* 17:637-642), progesterone is a promising candidate. Additionally, corticosterone is of particular interest because it is the primary hormone facilitating stress responses in birds and has the potential to participate in sex ratio manipulation at the level of the follicle; the adrenal gland, the primary site of corticosterone synthesis, is adjacent to the ovary and corticosterone is functionally important in maturation of the ovarian follicles and ovulation (Etches and Cunningham, 1976, *British Poultry Science;* 17:637-642). Indeed, hormonal manipulation of both corticosterone and progesterone produce significant biases in primary sex ratio. Previous studies showed that female biases are produced when maternal plasma levels of corticosterone are naturally high and experimentally elevated with implants (Bonier et al., 2007, *Behavioral Ecology;* 18:1045-1050; Pike and Petrie, 2006, *Proceedings of the Royal Society B-Biological Sciences;* 273:1093-1098). An acute treatment of female chickens with progesterone at the time of meiotic segregation induced a sex ratio skew towards females (Correa et al., 2005, *Biology Letters;* 1:215-218).

This study was designed to examine the effect of exogenous corticosterone and progesterone treatment at the time of meiotic segregation on offspring sex to determine if these hormones act at this critical time to influence offspring sex. Based on previous studies in other avian species, it is predicted that acute treatment of female zebra finches with either corticosterone or progesterone would stimulate the production of significantly more females. This is the first study to examine an acute injection of corticosterone on offspring sex ratios in birds.

Materials and Methods

Figure 3:
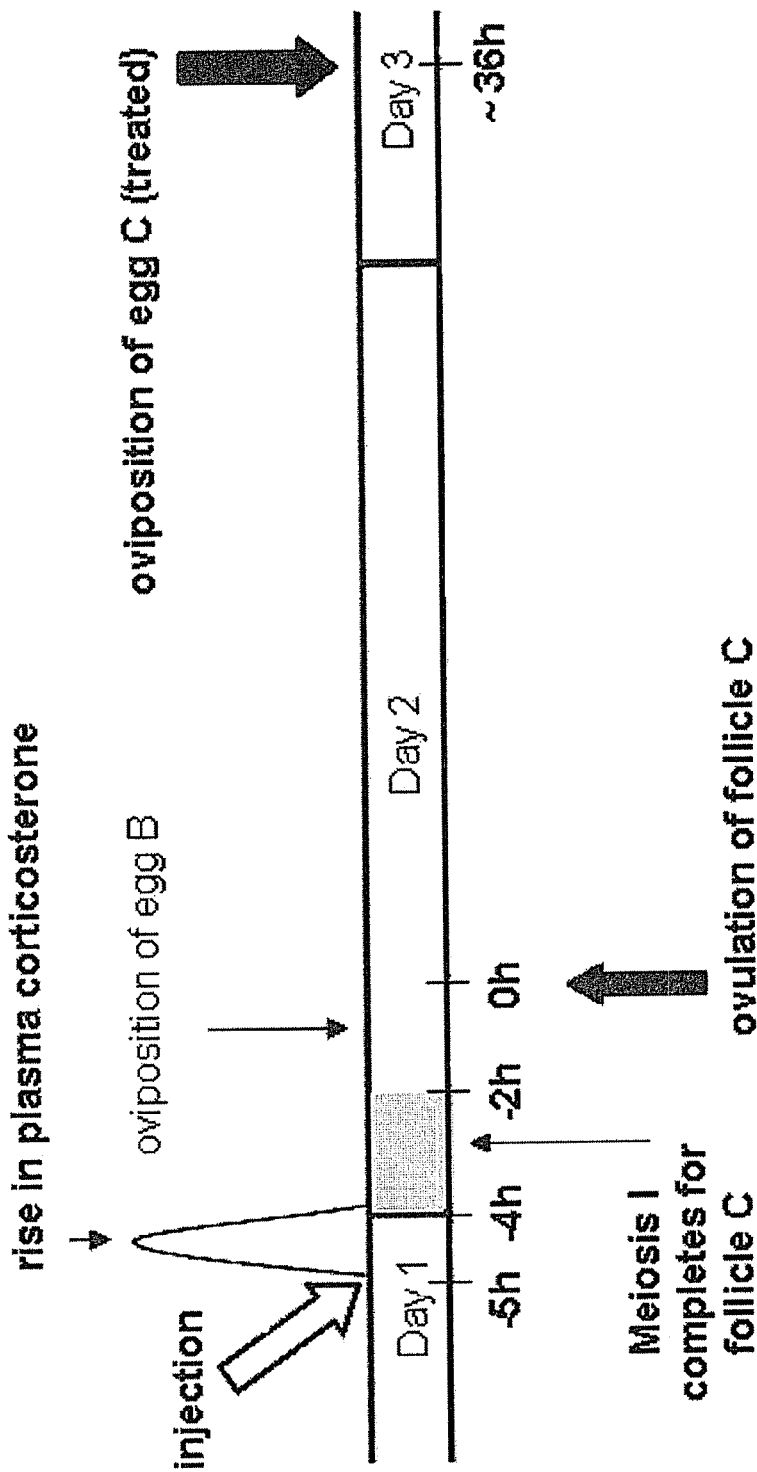
FIG. 3. Injections were timed to raise circulating corticosterone levels just prior to the period that meiosis I occurs. Meiosis I of the target follicle C occurs 2-4 hours before ovulation and ovulates (time 0) approximately 15-75 minutes after oviposition of egg B. The treated follicle C then precedes though the oviduct until oviposition approximately 36 hours after injection.

Zebra finch (*Taeniopygia guttata*) pairs obtained from a breeding colony maintained at The University of Georgia were housed in individual cages and provided feed and water ad libidumn. Birds were kept under a 14 hour (h) light (L):10 h dark (D) light schedule. Egg-laying was monitored daily and eggs marked to record sequence order. Females were injected intraperitoneally after the first or second egg of the clutch was laid with one of three treatments: 20 μg of CORT dissolved in 50 μl peanut oil and 10% ethanol (CORT), 20 μg of progesterone dissolved in 50.1 peanut oil and 10% ethanol (P), or 50 μl of control peanut oil (C). A fourth set of females received no injection treatment (UN). Injections were administered five hours before the predicted time of ovulation because previous work in chickens and quail suggests that meiosis I completes between 2 and 4 h prior to ovulation (Yoshimura et al., 1993, *Journal of Reproduction and Fertility;* 98:401-407). The follicle ovulating 5 hours after injection, was laid approximately 36 hours after injection (FIG. 3). Ovulating follicles exposed to treatments were laid as the 3rd or 4th egg in the sequence (3rd egg if treatment was administered on the day the 1st egg was laid and the 4th egg in the sequence if treatment was administered on the day the 2nd egg was laid). Eggs were allowed to incubate in the nest for 8-12 days prior to collection to allow sufficient embryonic development for DNA extraction and molecular sexing analyses. Occasionally these treatments disrupted the oviposition immediately following the injection. Females that delayed oviposition after treatment were excluded from analysis because it was not possible to determine whether the egg collected the following day was from the ovulation event that occurred immediately following injection or from a delayed oviposition of the follicle ovulated the day prior to injection. Females that delayed oviposition were allowed to complete the clutch after which the treatment was repeated during the next clutch. Progesterone treatment resulted in delayed oviposition of 5 eggs and no visible development was observed in another 4 eggs. Only 1/10 females treated with progesterone laid successfully. For this reason, progesterone treatments were eliminated from further analyses. Delayed oviposition and/or having no visible development was not more likely to occur in the CORT or control treatment groups relative to the one another or to uninjected controls, suggesting that the treatments employed by these groups did not trigger selective ovulation or reabsorption of ovarian follicles.

Molecular Sexing. Genomic DNA was extracted from embryonic tissue using a standard salt extraction method (Lambert et al., 2000, *Journal of Neuroscience Methods;* 95:127-132). Portions of the W-linked avian CHD (CHD-W) on females and its non W-linked homologue (CHD-Z) were amplified using polymerase chain reaction (PCR) with primers P2 and P8 (Griffiths et al., 1998, *Mol Ecol;* 7:1071-1075). PCR products were visualized on a 2.3% agarose gel stained with ethidium bromide. The presence of the W chromosome was determined through the visualization of two bands while males were identified when only one band was produced.

Radioimmunoassays. In a separate set of laying females, blood samples were taken at 20 minutes (min), 1 hour (h), and 2.5 h following the injection of CORT and control vehicle oil to verify that CORT treatment resulted in an elevation of plasma corticosterone. Different individuals were sampled at each time point. Blood samples were also taken from a set of unmanipulated females at time intervals 20 minutes and 1 hour, during the same bleeding session. To ensure that measurements reflect corticosterone elevations associated with the injection and not the stress of handling, samples were taken from the brachial vein within 3 minutes of capture (Romero and Romero, 2002, *Condor;* 104:129-135; Wingfield et al., 1982, *Condor;* 84:399-409). Injections and sampling began at 2300 hours (5 hors prior to ovulation) to accurately measure the blood plasma levels of corticosterone and changes in corticosterone levels in response to injections during the approximate period that meiosis occurs. Based on studies done in other avian species, it is likely that the time period from injection to blood sampling is just prior to the natural diurnal CORT peak that occurs at the end of the dark period (Westerhof et al., 1994, *Avian Diseases;* 38:428-434; de Jong et al., 2001, *Physiology and Behavior;* 74:299-304). The procedures for extraction and radioimmunoassay of corticosterone from plasma were followed as described by (Wingfield and Farner, 1975, *Steroids;* 26:311-327) and (Mendonça et al., 1996, *Horm Behav;* 30:153-161) using a rabbit derived anti-corticosterone antibody (MP Biomedicals, Solon, Ohio USA, cat #07-120016). The recovery rate of corticosterone from plasma was 91.5%. Intra- and inter-assay variations were 6.96 and 11.78 respectively.

Statistical Analysis. Plasma CORT concentrations were analyzed among treatment groups and time points using a two-way ANOVA, and individual treatment differences were analyzed using Fisher's PLSD. All hormone data were non-normally distributed and were thus log transformed for statistical analyses.

Twenty-one target embryos were successfully sexed from control females, 16 from non-injected females, and 18 from CORT treated females. Only eggs exposed to the treatment as ovarian follicles were used in this analysis, therefore only one egg the 3rd or the 4rd egg was used in this analysis. Differences in the number of females that produced males was analyzed among treatment groups by performing a logistic regression in StatView (SAS Institute, Cary, N.C. USA) using sex as the response variable (male=1). Chi square values derived from the logistic regression model are reported here. For untreated sex ratios, the 3rd egg of the clutch was used for analysis when both the 3rd and 4th egg was available because most treated eggs were from the 3rd position. Either 3rd or 4th eggs from the sequence were used, because the sex ratios between these two sequence positions do not differ when left untreated ($\chi 2=0.08$, $p=0.78$). Similar analyses were used to compare sex ratios from eggs produced before the target eggs within treatment groups. Posthoc power analyses using G*power 3 show that the sample sizes used in this study are sufficient when comparing single egg samples with proportional differences in sex ratios greater than or equal to 0.35 (Erdfelder et al., 1996, *Behavior Research Methods, Instruments, and Computers;* 28:1-11; Wilson and Hardy, 2001, Statistical analysis of sex ratios: an introduction. In: Hardy I (ed) Sex ratios: concepts and research methods, 1st edn. Cambridge University Press, New York, pp 48-92).

Results

Figure 4:
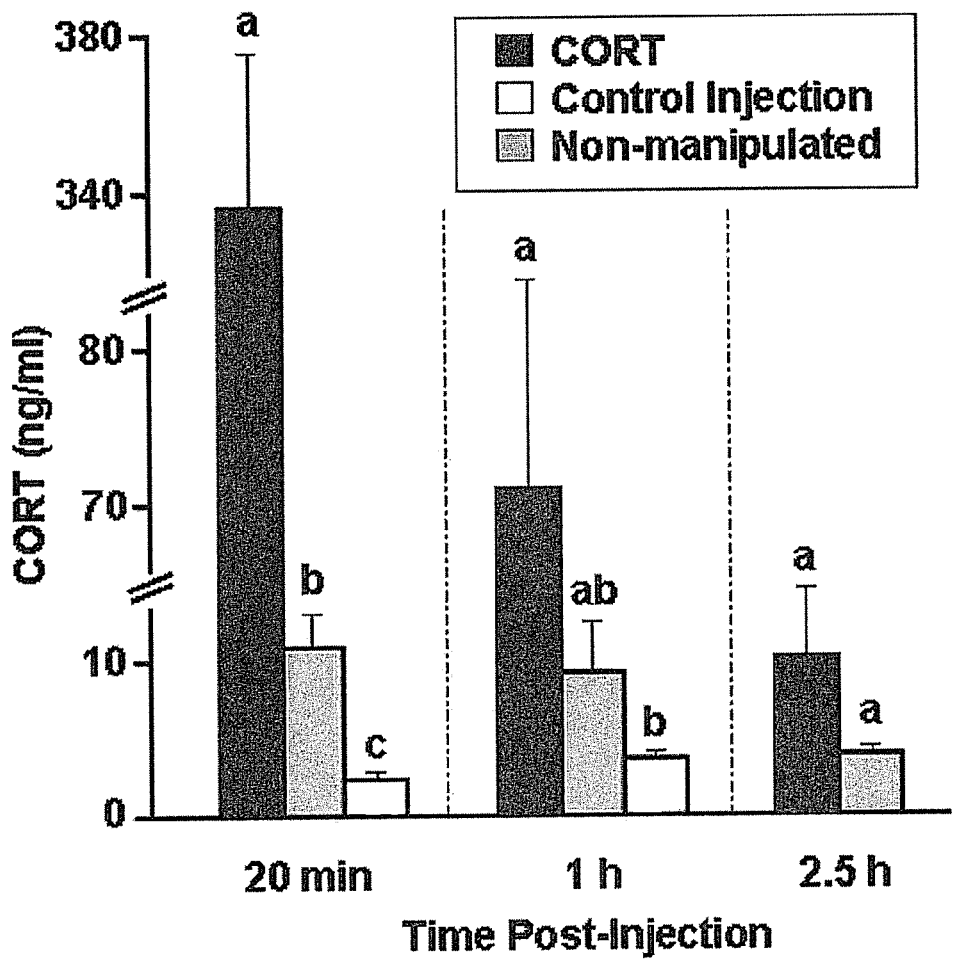
FIG. 4. Plasma corticosterone concentrations (mean+standard error) of female zebra finches injected with 20 µg corticosterone (N=10, 10, 7), oil (N=10, 9, 7) and non-manipulated females (N=9, 9). Plasma corticosterone levels were measured 20 min, one hour and 2.5 hours after injection of CORT and vehicle oil control. Comparison of corticosterone levels was analyzed between treatments at each time point and not between time points. CORT injections significantly raised plasma corticosterone levels min and one hour after injection. Control injections raised plasma corticosterone levels significantly 20 min after injection. All hormone measurements were log transformed for statistical analysis.

Blood samples taken 20 minutes and 1 hour after injection showed treatment had a significant effect on plasma CORT levels (FIG. 4; ANOVA, $F_{2,26}=150.84$, $p<0.0001$, $F_{2,254}=10.919$, $p<0.004$). Both CORT and C injections raised corticosterone levels significantly compared to non-injected birds 20 minute after injection (p<0.0001 in both cases). By 1 hour post-injection, corticosterone concentrations in control treated birds were no longer different from non-injected birds (p=0.4681) while levels in the CORT treated females remained significantly elevated (p=0.0002). Corticosterone levels were similar between control treated and CORT treated females 2.5 hours after injection ($F_{1,12}$=3.689, p=0.0789). Blood samples from non-manipulated females at 2.5 h post-injection were not taken. Blood samples were not taken from unmanipulated females at 2.5 h post-injection. Instead, CORT levels of unmanipulated birds 1 h post-injection were compared to corticosterone levels of control and CORT treated birds at 2.5 hr post-injection ($F_{2,22}$=2.759, p=0.0853). At 2.5 hr post-injection, CORT treated birds still had significantly higher corticosterone levels compared to unmanipulated females (p=0.0401) while C injected birds had similar corticosterone levels as unmanipulated birds (p=0.886).

Figure 5:
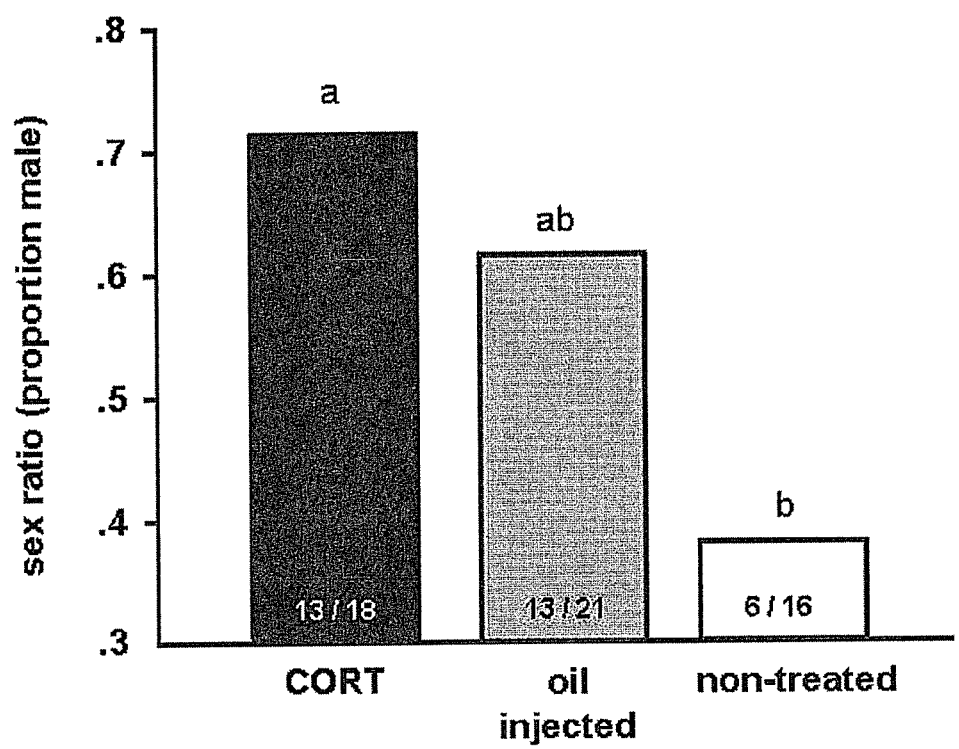
FIG. 5. Primary sex ratio (proportion of male embryos) in offspring of corticosterone-injected, control-injected and non-manipulated zebra finch females. Corticosterone injected females produced significantly more male embryos than non-manipulated females. Primary sex ratios was did not differ significantly between corticosterone injected and control injected females or between non-manipulated and control injected females.

Females treated with CORT produced significantly more males (72%) compared to unmanipulated controls (37.5%), (CORT $\chi2$=3.955 p=0.046) (see FIG. 5 and Table 1). When comparing sex ratio of eggs before the target eggs, there was no bias in the offspring sexes produced among treatment groups (CORT-C before $\chi2$=0.038, p=0.84, CORT-UN before $\chi2$=0.616, p=0.251, C-UN before $\chi2$=0.117, p=0.7325), suggesting that targeted treatment was the factor affecting the sex ratio biases observed.

TABLE 1

Primary sex ratio of offspring in the target eggs and the eggs laid prior to treatment produced by corticosterone-treated, control-treated, and untreated females.

| Relative egg position | Treatment | Total number of embryos sexed | Proportion male |
|---|---|---|---|
| Before treatment | corticosterone | 16 | 0.4375 |
|  | control injection | 24 | 0.4167 |
|  | non-injected control | 20 | 0.45 |
| Treatment | corticosterone | 18 | 0.72 |
|  | control injection | 21 | 0.619 |
|  | non-injected control | 16 | 0.375 |

Discussion

The results of this example show that exogenous administration of a pharmacological dose of corticosterone just prior to the onset of sex chromosome segregation stimulates a sex-ratio skew towards males. Multiple studies have pointed to the potential for hormonal control of primary sex ratio through non-random segregation of sex chromosomes during meiosis I (Krackow, 1995, *Biol Rev Camb Philos Soc;* 70:225-241; Pike and Petrie, 2003, *Biol Rev;* 78:553-574; and Rutkowska and Badyaev, 2008, *Proc R Soc Lond Ser B-Biol Sci;* 363:1675-1686). Even though the exact timing of meiotic segregation has not been qualified in zebra finch, we know that meiotic segregation occurs within the 5 hour time period between injection and ovulation because our injection experiment resulted in an effect on sex ratio. This example is the first study to examine the effects of acute corticosterone administration at sex chromosome segregation.

Recent studies examining the effects of corticosterone on primary sex ratio showed a female bias when blood plasma levels were artificially elevated with corticosterone implants and in females with naturally higher base line CORT levels (Pike and Petrie, 2006, *Proc R Soc Lond Ser B-Biol Sci;* 273:1093-1098; and Bonier et al., 2007, *Behav Ecol;* 18:1045-1050). However, in each of these cases, corticosterone elevations that stimulated sex ratio skews towards females were chronic, long-term elevations. Perhaps chronic corticosterone elevations act on offspring sex through a different mechanism compared to acute elevations. For example, corticosterone may act directly on the follicle when elevated acutely during meiotic segregation, but indirectly when elevated chronically through the modulation of other hormones and factors, that subsequently influence offspring sex. Chronic corticosterone elevations could also act by depressing the amount of yolk precursors available during follicular growth for the rapid yolk deposition phase. In chickens and zebra finches, exogenous corticosterone treatment through implants reduces that amount of yolk precursors and depression of follicular growth during the period of rapid yolk deposition (Salvante et al., 2003, *Integr Comp Biol;* 43:849-849; and Salvante and Williams, 2003, *Gen Comp Endocrinol;* 130:205-214) and it has been suggested that the rate of follicular growth may influence meiotic segregation such that more of one sex is produced (Young and Badyaev, 2004, *J Evol Biol;* 17:1355-66). Alternatively, perhaps chronic corticosterone elevations down-regulate corticosterone receptors on the oocyte (Kwok et al., 2007, *Poult Sci;* 86:423-430) that would normally trigger a male-bias in response to an acute elevation such as the one shown here. Future studies will need to investigate the mechanisms by which chronic and acute corticosterone exposure produce opposite results on offspring sex ratios in this species.

In comparison to other studies documenting primary sex ratios, this example found similar sex ratios to those reported in unmanipulated zebra finch colonies (40%) (Kilner, 1998, *Animal Behavior;* 56:155-164). Additionally, in a study that injected White Leghorns chickens with a control oil vehicle prior to meiosis 1 they found a sex ratio of 61-63% (Correa et al., 2005, *Biology Letters;* 1:215-218) similar to the sex ratio observed in the control injected group. The lack of a difference in offspring sexes produced between the CORT and control treated groups could indicate that the injection protocol itself was partially responsible for the sex ratio biases seen here. However, the fact that the CORT treated females produced significantly more males compared to the uninjected treatment group while the control treated females did not suggests that corticosterone may be responsible for the effect observed. Peanut oil was purposefully chosen for the current experiment because of its innocuous nature, and because it does not contain the phytoestrogenic qualities of other oils (e.g. sesame oil) commonly used in similar experiments (Thompson et al., 2006, *Nutrition and Cancer;* 54:184-201). Further, given that corticosterone levels were significantly elevated in the control treated females, it seems likely that these elevations in corticosterone concentrations may also be responsible for the male bias (though not significant) compared to un-injected females. Future studies that employ physiological stressors in an acute manner are necessary to test this.

This example demonstrates that sex manipulation can clearly occur exclusively through hormonal manipulation at the time of meiotic segregation, lending insight into mechanisms that may be responsible for sex ratio adjustment in birds.

Example 3

Acute Corticosterone Administration Stimulates a Male-Biased Sex Ratio in Laying Hen Birds have demonstrated a remarkable ability to manipulate offspring sex. Previous studies suggest that treatment with hormones can stimulate females to manipulate the offspring sex prior to ovulation. Specifically, chronic treatments with corticosterone, the primary stress hormone produced by birds, stimulated significant skews towards female offspring. It has been suggested that corticosterone acts by influencing which sex chromosome is donated by the heterogametic female bird into the ovulated ovarian follicle. However, it is difficult to pinpoint when its effects on offspring sex occurred because corticosterone treatment occurred over a long period of time. This example treated laying hens with acute high-dose corticosterone injections five hours prior to ovulation and quantified the sexes of the subsequently ovulated eggs to test whether an injection of corticosterone coincident with segregation of the sex chromosomes would stimulate hens to produce more female than male offspring. Contrary to this prediction, hens injected with corticosterone produced a significant bias towards male offspring, nearly 83%. These results suggest that acute corticosterone during meiosis I may mediate primary sex ratios in birds. Furthermore, acute corticosterone exposure, compared with chronic exposure, may act through different mechanisms to skew offspring sex.

Biases in avian primary sex ratios have been documented in relation to a variety of social and environmental conditions (reviewed in Pike and Petrie, 2003, *Biol Rev;* 78:553-574; Alonso-Alvarez, 2006, *Poul Avian Biol Rev;* 17:1-20); however, little is known about the mechanism controlling these primary sex ratios. Female birds likely control offspring sex prior to ovulation because the female is the heterogametic sex, contributing either a W or Z chromosome to offspring. Sex of the offspring is determined 2-4 hours prior to ovulation during the first meiotic division when one sex chromosome is retained in the oocyte and the other segregates to the polar body (Olsen and Fraps, 1950, *J Exp Zool;* 144:475-487; Johnson, 1996, *Poul Avian Biol Rev;* 7:99-110). Hence, it has been suggested that females can manipulate the sex of their offspring prior to oviposition, possibly by non-random segregation of sex chromosomes during the first meiotic division (Krackow, 1995, *Biol Rev;* 70:225-241; Pike and Petrie, 2003, *Biol Rev;* 78:553-574; Alonso-Alvarez, 2006, *Poul Avian Biol Rev;* 17:1-20).

Hormones may be mediators in the mechanism of sex ratio manipulation. Corticosterone, the primary stress hormone in birds, is of particular interest because the left adrenal is embedded in the ovary, suggesting the potential for mediation of follicular maturation and other ovulatory processes. Indeed, corticosterone is elevated during and necessary for ovulation (Etches and Cunningham, 1976, *Br Poult Sci;* 17:637-642).

Studies in other avian species suggest that chronically elevated corticosterone in breeding females biases the primary sex ratios towards females (Pike and Petrie, 2005, *Anim Behav;* 70:745-751; Pike and Petrie, 2006, *Proc R Soc Lond B;* 273:1093-1098; Bonier et al., 2007, *Behav Ecol;* 18:1045-1950). In these studies, corticosterone was elevated over the entire ovulatory process, making it difficult to pinpoint when corticosterone was playing a role in sex ratio manipulation.

This example determined the effect of acute, exogenous corticosterone treatment at the completion of meiotic segregation to determine if corticosterone acts during that time to influence offspring sex.

Materials and Methods

Hyline W-36 and Brown layer hens were housed in individual layer cages in a single room, had ad libitum access to food and water, and maintained on a 14 h L:10 h D light schedule. Hens were artificially inseminated biweekly with pooled semen from 8 roosters to ensure egg fertilization. Hens were monitored throughout the day for egg-laying and eggs were collected manually every 2 h during peak-laying hours. Previous studies in laying hens have shown that ovulation occurs within 30 minutes of oviposition (Johnson, A. L. Reproduction in the female, in Sturkie's Avian Physiology. G. C. Whittow, Editor. 2000, Academic Press: New York, N.Y. p. 569-596); therefore, egg laying patterns can be used to predict the timing of ovulation.

Figure 6:
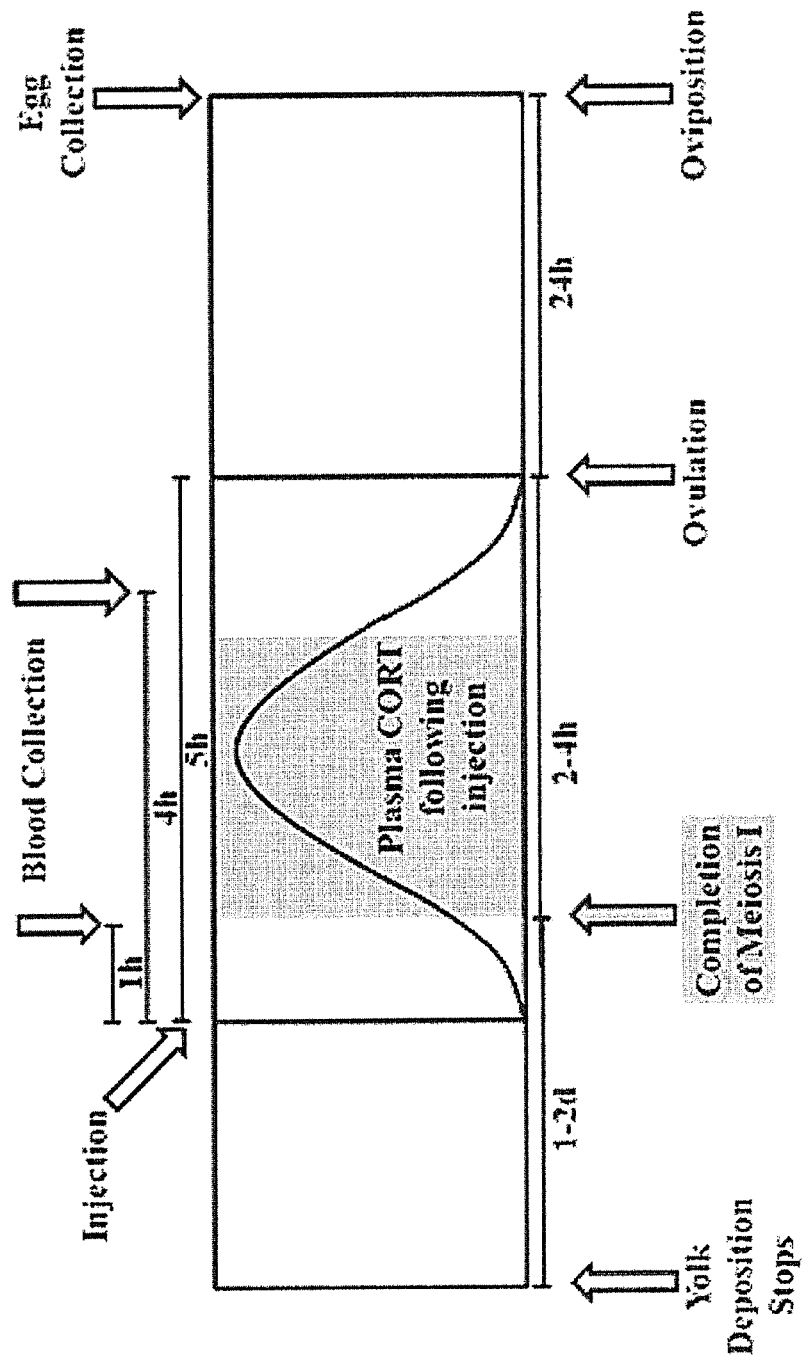
FIG. 6. Injections were timed to elevate corticosterone during the completion of Meiosis I. Blood samples were collected one and four hours after injection and the target egg was collected approximately 29 hours after injection.

Injection treatments were administered to hens subcutaneously in the back of the neck five hours prior to the predicted time of ovulation with one of the following treatments: 0.5 ml of control peanut oil (CONT) or 1.5 mg corticosterone dissolved in 0.5 ml of peanut oil (CORT). Ovulated follicles took 24 h to pass through the remainder of the reproductive tract and were collected at oviposition (FIG. 6). Eggs were also collected on the day prior to injections and were considered the unmanipulated group (UN). Neither the control nor the corticosterone treatment had an effect on ovulation or oviposition rates. Eggs were incubated for 10 days at 37.5° C. and 58% relative humidity in a Natureform incubator.

Molecular sexing. Embryos were manually removed from eggs and genomic DNA was extracted from embryonic tissue using a standard salt extraction method (Lambert et al., 2000, *J Neurosci Meth;* 95:127-132). Portions of the W-linked avian CHD (CHD-W) in females and the non W-linked homologue (CHD-Z) were amplified using polymerase chain reaction (PCR) with primers 2550F and 2718R (adapted from Fridolfsson and Ellegren, 1999, *J Avian Biol;* 30:116-121). For PCR amplification, a reaction volume of 20 ul was used, containing 0.7 ul $MgCl_2$, 2 ul 10× iTaq buffer, 0.4 ul dNTP, 0.2 ul each primer, 0.13 ul iTaq polymerase, 1 ul DNA, and water. Reaction parameters were the same as those described in Fridolfsson and Ellegren 1999. PCR products were visualized on a 3% agarose gel stained with ethidium bromide. Thirty-two embryos were sexed from UN-treated females, 16 from CONT-treated females, and 23 from CORT-treated females.

Radioimmunoassays. Blood samples were collected from a separate set of hens to verify that CORT treatment elevated plasma corticosterone during the completion of meiotic segregation. Relative to the injections described above (5 h prior to ovulation), blood samples were collected from half of the CORT, CONT, and UN-treated hens at 1 h and the other half at 4 h (FIG. 6). Blood samples were collected from the brachial vein within 3 min of initial handling to avoid variation due to handling stress (Romero and Reed, 2005, *Comp Biochem Physiol A;* 140:73-79). Extraction and radioimmunoassay of plasma corticosterone were completed as described by Mendonça et al. (Mendonça et al., 1996, *Horm Behav;* 30:153-161). Twenty-four blood samples were analyzed from UN-treated hens (12 from each time period), 12 from CONT-treated hens (5 and 7 at 1 h and 4 h, respectively), and 12 from CORT-treated hens (6 from each time period).

Statistical Analysis. Logistic regressions using sex as the response variable (male=1) were used to analyze data in two ways. First, sexes of eggs produced by each treated group (CONT and CORT) were compared to all of the eggs produced by the same hens the day before (UN) to determine overall treatment differences among the three groups and maximize sample sizes. Second, pre-treated hens were split into the treatments they later received (CORT or CONT) and offspring sexes were compared to determine whether hens changed the sexes produced in response to the treatments. All hormone data were non-normally distributed and were log-transformed for statistical analysis. Plasma corticosterone concentrations were analyzed among treatment groups and time points using an ANOVA and differences among individual treatment groups were analyzed using Fisher's PLSD. Statistical analyses were carried out using Statview software (SAS Institute, Cary, N.C. USA).

Results

Females treated with corticosterone produced 82.6% males, significantly more than were produced by all hens the day before ($\chi2=6.56$, $p=0.01$) but not significantly more males than those produced by hens receiving control injections ($\chi2=0.13$, $p=0.72$). While females receiving a control injection produced a slightly male-biased sex ratio, this was not statistically different from sex ratios produced by all hens the day before ($\chi2=1.93$, $p=0.17$) (FIG. 7A).

Overall, when combining CORT and CONT injected females, there was no difference in the sex ratios produced between pre-target and target eggs ($\chi2=0.13$, $p=0.72$). However, when CORT and CONT treated females were separated, females produced significantly more males after treatment with corticosterone, but not with the control vehicle, compared to before treatment (FIG. 7B, CORT: $\chi2=5.56$, $p=0.02$, CONT: $\chi2=0.64$, $p=0.42$).

Figure 7:
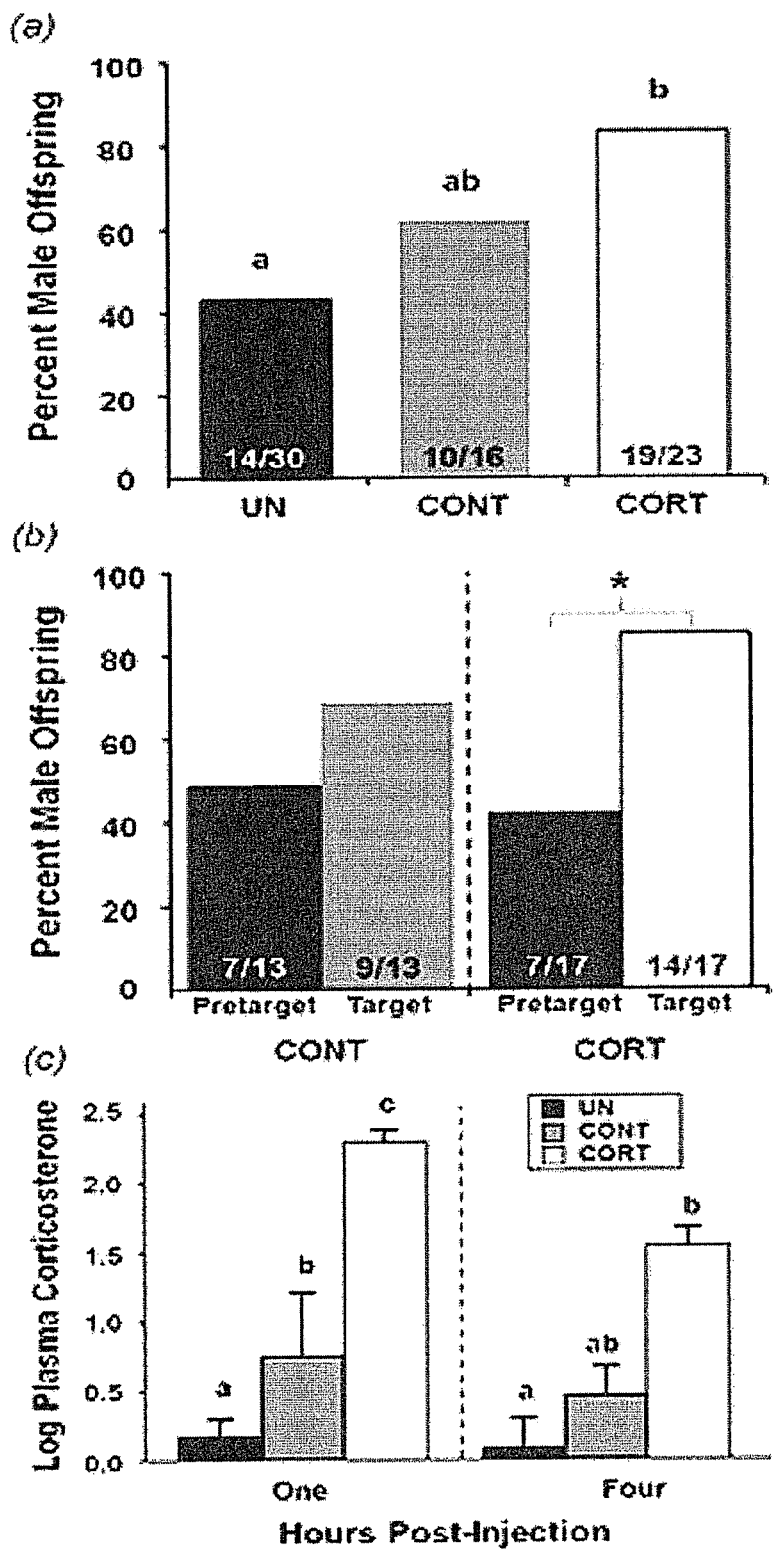
FIG. 7. Comparison of percentage male offspring produced among CONT, CORT, and UN-treated hens (FIG. 7A) and between pre-target and target eggs from the same hens (FIG. 7B). Ratios shown in bars represent ratios of males to total offspring.

Blood samples collected from a separate set of hens 1 h and 4 h after injection showed that a surge of corticosterone was induced in CORT-treated hens (FIG. 7C; 1 h:$F_{2,20}=33.30$, $p<0.0001$; 4 h:$F_{2,23}=4.32$, $p<0.05$). CORT injections significantly raised corticosterone levels compared to CONT and UN treated hens 1 h after injection ($p<0.0001$ in both cases). CONT treatment also significantly raised corticosterone levels compared to UN treated females one hour after injection ($p<0.05$), suggesting that the injection and handling method induced a handling stress in the hens. By four hours post-injection corticosterone concentrations were only significantly elevated in CORT-treated hens (CORT-UN: $p<0.01$, CORT-CONT: $p=0.07$, CONT-UN: $p=0.33$).

Discussion

Contrary to an original hypothesis that acute corticosterone treatment during meiotic segregation would skew offspring sex ratios towards females, the results of this example show that exogenous administration of a pharmacological dose of corticosterone stimulates a significant sex ratio skew towards males. Moreover, while sex ratios produced by CORT-treated hens differed from those produced by UN-treated hens, there was no difference between ratios produced by CORT and CONT-treated hens.

These results differ from those of recent studies in other avian species that show a female bias when corticosterone plasma levels were chronically elevated with corticosterone implants or chronic stress (Pike and Petrie, 2005, *Anim Behav;* 70:745-751; Pike and Petrie, 2006, *Proc R Soc Lond B;* 273:1093-1098; Bonier et al., 2007, *Behav Ecol;* 18:1045-1950), but concur with the study in zebra finches showing a male-bias after acute treatment with corticosterone, presented in Example 2. Perhaps acute and chronic corticosterone elevations differentially regulate a similar mechanism. For example, chronic exposure to corticosterone can down-regulate the expression of corticosterone receptors (Meyer et al., 2001, *Hippocampus;* 11:329-336). In this way, chronic exposure to corticosterone could inhibit the acute actions of corticosterone that would normally stimulate the production of males. Alternatively, perhaps acute and chronic elevations act through other hormones in different ways. Chronic corticosterone elevations are known to influence other hormones that have been shown to affect offspring sex in birds, such as progesterone or testosterone (Correa et al., 2005, *Biol Lett;* 1:215-218; Rutkowska and Cihon, 2006, *Anim Behav;* 71:1283-1288; Goerlich et al., 2009, *Gen Comp Endocrinol;* 163:184-192) and could act by influencing or down-regulating these hormones over time. In the acute sense, corticosterone may act directly on the developing follicle, as glucocorticoid receptors and enzymes that metabolize glucocorticoids have been identified in the avian ovary (Kucka et al., 2006, *Gen Comp Endocrinol;* 147:377-383). It is possible that the pharmacological nature of the injection produced different effects compared to a physiological dose. Further research needs to be conducted so these possibilities can be tested.

While it is possible that a factor related to the injection procedure itself drove the sex ratio changes observed, this is unlikely given that sexes produced by the CONT group were not statistically different from the UN group while sexes from the CORT group were. Instead, there may be a dose-dependent response to corticosterone elevation, since the CONT group experienced significant corticosterone elevation. The effects of high physiological doses of CORT must be tested.

The results of this study suggest that corticosterone exerts an influence on offspring sex at the point of meiotic segregation. Whether corticosterone acts directly on the follicle or plays an indirect role remains to be determined. To our knowledge, this is the first study to examine the effect of an acute elevation of corticosterone on offspring sex ratios in the domestic hen and it provides insight into the possible mechanisms controlling sex ratio manipulation in birds.

Example 4

Effects in Zebra Finches of Acute Physiological and Pharmacological CORT Exposure in the Presence and Absence of a CORT Antagonist In Vivo Zebra finches, *Taeniopygia guttata*, are small passerines that have particular aptitude for primary sex ratio manipulation, skewing offspring sex ratios in relation to environmental and social variables, including laying order, mate attractiveness, and diet quality and quantity. Zebra finches are socially monogamous and breed year-round in an opportunistic manner. Because they are easy to maintain in captivity, much work has been done with zebra finches and they remain one of the few avian species for which the entire genome has been sequenced. Additionally, all hormone assays and genetic sexing analyses to be used here have been validated for zebra finches. In Examples 1 and 2, the acute stress of the control injection occurred at 5 h prior to ovulation. CORT concentrations rose significantly within 20 min but declined again within 1 h. In addition, the polar body extrusion likely occurs 2-4 h prior to ovulation. This means that the effect of the stress likely took place within 160 min of the injection This example will determine whether the effects observed in Examples 1 and 2 were due to the pharmacological nature of the CORT dose given and whether CORT action can be blocked by a CORT antagonist, RU486. Female zebra finches in this experiment will be randomly distributed to one of seven treatment groups (n=30 in each). Two of the groups will receive a pharmacological dose of CORT (20 ug) dissolved in peanut oil, two will receive a physiologically high dose (1 ug, 15× lower than that used in Examples 1 and 2), and two will receive a control injection of vehicle (peanut oil) only. To test whether CORT is a mediator in the sex determination process, one group from each of these treatment sets will also receive a dose of RU-486 (0.5 mg dissolved in 50 ul $dH_2O$), a glucocorticoid receptor blocker, administered 15 min prior to the injection treatment itself (dose and timing based on. While RU-486 plays a dual role, acting as a progesterone receptor antagonist, in mammals, the chicken progesterone receptor does not bind to RU-486 due to a single amino acid substitution. Analysis of the zebra finch genome shows that zebra finches share the same amino acid substitution, eliminating the complication of progesterone receptor binding to RU-486 in this species. One final group will receive no injection treatment.

Injections will take place 5 h prior to ovulation (as above) which produces a CORT peak prior to the natural CORT peak that occurs just prior to lights on. After the injections, females will be returned to their home cages and oviposition will be monitored rigorously through the nesting cycle, laying order will be marked, and eggs will be collected after 2 d of incubation for molecular sexing of embryos. Sexes of target and non-target eggs will be compared among treatment groups. In addition to sex ratios, yolk will be collected from all eggs to determine yolk CORT and testosterone concentrations. Blood will also be sampled from a subset of females (n=12) (from which sex ratios will not be collected), to measure CORT and testosterone levels as well. This experiment will test whether a pharmacological dose of CORT is necessary to skew sex ratios and whether CORT is truly an involved mediator.

It is expected that the pharmacological dose of CORT will induce a male-biased sex ratio. If a physiological dose is sufficient to alter sex ratios, a male bias will be seen in this group as well. If a biased sex ratio is not seen in the physiological treatment group, it may be that the dose is insufficient to induce either the direct or indirect effects necessary, or that pharmacological and physiological doses are acting through different receptors.

If the pharmacological and/or physiological doses of CORT stimulate and effect sex ratio as a result of glucocorticoid receptor (GR) activation, treatment with RU-486 should block this effect. If RU-486 does not block this effect, then the effect may instead occur through activation of MRs. If RU-486 does not inhibit CORT induced sex ratio skews, an additional group of birds will be added, birds treated with fludrocortisone (0.3 mg in 50 ul peanut oil), which is an MR agonist for which GRs have a very low affinity.

Given that the act of a control injection itself produces a corticosterone increase, a male bias may be seen in the control treatment group. For this reason, the un-injected group to used as a comparison as well.

If the physiological dose of CORT does not induce an effect on the sex ratio, it is possible that, rather than being too low, this dose is metabolized too quickly and does not affect the follicle at exactly the right time. Thus, if an effect of the physiological CORT dose is not seen, the dose will be provided one hour later such that the elevation of CORT extends through the period that the elevation produced by the pharmacological dose does.

As in Example 1 and 2, it is predicted that high and low dose CORT treatment will induce an increase in CORT and testosterone concentrations, while control treatment will induce only a mild increase in CORT. In addition, it is expected that yolk CORT and testosterone will also increase as well. Increases in these hormones in yolk would provide evidence that the GD is directly exposed to higher concentrations of these hormones in response to our treatments.

Example 5

Effects of Acute Corticosterone Administration with an Androgen Receptor Antagonist on Sex Ratios in Zebra Finches In Examples 1 and 2 it was found that within 1-3 hours of administration of a pharmacological dose of CORT, testosterone concentrations increased significantly. It is possible that the effects of this injection on sex ratios occurred in an indirect manner through the actions of testosterone. Indeed, treatment with testosterone induced a skew towards males in zebra finches and pigeons. The following experiments will address this possibility.

Breeding female zebra finches will be distributed into one of five treatment groups (n=30 each). One group will receive an injection containing a pharmacological dose of corticosterone that was shown in preliminary experiments to both skew sex ratios towards males and significantly increase testosterone concentrations (20 ug of CORT in 50 ul peanut oil). The second group will receive 50 ul peanut oil containing the same dose of CORT as well as 1 mg of the androgen receptor antagonist flutamide. This treatment should block effects that result solely from the testosterone elevation that occurs after CORT injection. The third treatment will receive an injection of testosterone only (20 ug dissolved in peanut oil). The fourth treatment group will receive a control oil injection and the fifth will receive no treatment. All injections will be given 5 h prior to ovulation as above, after which all females will be returned to their home cages and oviposition will be monitored rigorously through the nesting cycle. Laying order will be marked, and eggs will be collected after 2 d of incubation for molecular sexing of embryos, after which sexes will be compared among groups.

If testosterone is the factor responsible for stimulating sex ratio skews after treatment with CORT, inhibition of a testosterone increase using flutamide will inhibit the male biased sex ratio skew induced by CORT treatment. In addition, treatment with only testosterone in the absence of CORT should induce a male biased sex ratio if testosterone is the sole factor involved.

Example 6

The Roles of Maternal Stress and Corticosterone in Offspring Sex Ratio Adjustment in Leghorn Chickens This example will determine the mechanism by which corticosterone is acting on offspring sex ratios with an ultimate goal of developing either a very short-term hormonal or a non-hormonal treatment by which offspring sex can be purposefully controlled. First, this example will determine at what point in the process of follicular development CORT affects sex ratios, as well as the duration of CORT elevation required for sex ratio adjustments to occur (Experiments 1 and 3). Using experiments that address those questions, this example can also assess two potential mechanisms by which CORT acts: Direct manipulation of meiotic segregation (Experiment 4) or indirect influences on segregation through depression of follicular growth (Experiment 2).

Previous studies in quail, white-crowned sparrows, pea fowl, and a preliminary study conducted in zebra finches have shown that long-term elevation of circulating CORT concentrations skewed sex ratios towards females (Bonier et al., 2007, *Behavioral Ecology;* 18:1045-50; Love et al., 2008, *Hormones and Behavior;* 53:104-11; Pike and Petrie, 2005, *Biology Letters;* 1:204-7). This has not been previously tested in chickens, however given the pervasiveness of these effects in a wide range of species, as well as the fact that the effects of acute CORT on sex ratio was also similar in both chickens and finches suggests that chronic CORT elevation should stimulate sex ratio skews towards females in chickens as well. This example will examine the effects of both chronic stress-induced and exogenous elevations of CORT on offspring sex ratios, laying patterns, as well as on blood concentrations of CORT and other hormones known to change in response to CORT and act on processes of ovarian follicular development.

Experiment 1A

Effects of Chronic Stress on Offspring Sex Ratios

The chronic stressor chosen for this experiment is a repeated restraint stress that takes place three times daily for 2 weeks. Ladewig suggested that chronic intermittent stress is the best way to simulate chronic stress in animal models. See Ladewig, J. Chronic intermittent stress: a model for the study of long-term stressors. In: Biology of animal stress: basic principles and implications for animal welfare, Wallingford/London: CABI publishers; 2000, p. 159-70. And, previous work using this repeated restraint technique at a lower magnitude in leghorn chickens showed that restrained hens maintained significantly higher CORT concentrations for over a week before becoming habituated to the stress regime (Beuving and Vonder, 1978, *General and Comparative Endocrinology;* 35:153-9; Downing and Bryden, 2008, *Physiology and Behavior;* 95:381-7). Laying hens in this experiment will be randomly distributed into to one of two treatment groups: (1) the chronic stress group, which will be repeatedly restrained by wrapping tightly in a cloth such that the wings are pinned to the body for 10 minute periods three times per day for 2 weeks, and (2) a control group where hens remain unhandled and undisturbed (except for feeding periods) for the same two week period. Stress treatments will take place 2, 4, and 6 h after ovulation so as not to interfere with ovulatory processes of the following follicle, however previous studies have shown that chronic intermittent stress (restraint in particular) results in an overall elevation of baseline CORT levels, simulating a chronically stressful situation. Blood samples will be taken from stressed birds following the completion of each stress challenge and from a separate set of undisturbed hens (which will not be part of later sex ratio analyses) at the same times during the day for comparison. In addition, blood samples will also be taken from a subset of the stressed and control birds at 4 and 6 h prior to ovulation (when birds will not be undergoing a stress response but should exhibit elevated baseline CORT levels indicative of chronic stress). CORT as well as hormones known to change in response to CORT and play a role in ovarian follicular processes—testosterone, progesterone, and leptin—will be measured in blood samples. Finally, CORT concentrations will be measured in the yolk of each collected egg as well.

For the duration of this experiment, hens will be artificially inseminated biweekly using pooled semen from 10 roosters. Fertilized eggs will be collected from stressed and control birds 4, 7, and 13 days following the onset of the stress treatments. Eggs will be incubated for 2 d and embryos will be separated and sexed using molecular techniques described above in the detailed methods section. Two days of incubation is the shortest amount of time producing sufficient embryonic development for DNA isolation and accurate sexing analyses (see detailed methods below). Sex ratios and yolk CORT as well as circulating plasma concentrations of CORT, testosterone, leptin, and progesterone will be analyzed in relation to the two treatment groups, as well as in relation to laying position.

Experiment 1

B Effects of Chronic Exogenous CORT Elevation on Offspring Sex Ratios

Laying hens in this experiment t will be randomly distributed to one of two treatment groups (n=40 in each): (1) A CORT implant treatment group, which will receive a 1-inch silastic implant containing crystalline CORT or (2) a control group receiving an empty control implant. Females will be artificially inseminated using pooled semen from 10 roosters biweekly for 4 weeks. Oviposition will be monitored daily, laying time recorded, and fertilized eggs will be collected 4, 7, and 13 d following implantation and incubated for 2 d to allow minimal embryonic development. Embryos will be isolated and sexed using PCR-based molecular techniques described above.

Additionally, concentrations of CORT and three other hormonal factors known to interact with CORT and ovarian follicular development—testosterone, progesterone, and leptin—will be measured in blood samples taken 4 h after ovulation as well as 4 and 6 h prior to ovulation in females from both treatment groups on days 3, 6, and 12 (to correspond with ovulation of collected eggs above). CORT concentrations will be measured in the yolk of each collected egg as well. In preliminary studies, similar silastic CORT implants significantly elevated CORT concentrations within 2 d of implantation, and this elevation persisted when measured 1 week following implantation. Additionally, laying patterns were monitored for 2 weeks following implantation and 100% of birds implanted with CORT implants continued to lay at a similar frequency compared to before implantation, illustrating that we will be able to collect eggs from birds following this chronic implant treatment.

It is expected that the results of Experiments 1A and 1B will indicate: females in the chronic stress and CORT implant groups will have significantly elevated circulating CORT concentrations compared to control and control implant females; offspring sex ratios will be significantly more female biased in the chronic stress and CORT implant group compared to the control and control implant groups; and because elevated CORT levels have been shown to stimulate decreases in testosterone and leptin and increases in progesterone concentrations in birds, it is expected that birds in the chronic stress and CORT implant groups will have significantly lower levels of testosterone and leptin and higher levels of progesterone compared to controls.

Experiment 2

Effects of CORT Exposure and Maternal Stress History on Follicular Growth as it Relates to Offspring Sex Ratio This experiment will be conducted on yolks collected from eggs during Experiments 1a and 1b, in which birds experienced chronic stress and/or chronic CORT elevation. This is because the majority of follicular growth, characterized by the rapid yolk deposition phase stops 24-48 h prior to ovulation. Thus, acute stress and injection treatments would not alter follicular growth rates. Because all eggs for all experiments will be collected after only 2 d of incubation, the yolks should still be relatively intact. Yolks will be frozen upon collection sectioned into a 2 mm slice. Follicular growth will be calculated by staining yolk rings according to methods described in Young and Badyaev (Young and Badyaev, 2004, *J Evolutionary Biol;* 17:1355-66). This method provides a measure of follicular growth rate during the period of rapid yolk deposition as well as a total time of follicular growth based on the number of yolk rings. To verify that the two day period of incubation does not change the yolk ring layering, subsamples of freshly collected yolks under the chronic stress conditions will be initially compared to those of yolks that have undergone initial embryonic development. Growth rates and periods from chronically stressed and CORT treated birds will be compared to those from control birds, and growth rates will also be compared with the sexes of embryos collected from the same eggs. Sexes will be coded as 0 for female and 1 for male, and sexes will be analyzed in relation to follicular growth rate using a logistic regression. This experiment will determine whether chronic stress and CORT implants depress follicular growth, and whether follicular growth relates to offspring sex in this species.

Because CORT decreases the availability of yolk precursors in birds (Salvante et al., 2003, *General and Comparative Endocrinology;* 130:205-14), it is expected that growth rates of follicles collected from chronic stress and CORT implant treatment groups will have significantly lower growth rates, and significantly longer development periods compared to eggs collected from control and control implant groups.

If follicular growth rate alters processes of meiotic segregation, it is expected that embryos collected from eggs that had faster follicular growth rates will more likely be male compared to those collected from eggs that had slower follicular growth rates.

As shown in the previous examples, a pharmacological dose of CORT at meiotic segregation skewed sex ratios significantly towards males. It is now necessary to determine whether this effect is dose-dependent, and how acute CORT exposure affects offspring sex at different stages of follicular development. Two proposed experiments have been designed to address this hypothesis:

Experiment 3A

Effects of Exposure to an Acute Stressor on Offspring Sex Ratios

Laying hens will be randomly distributed to one of three treatment groups (n=40 in each): Two of the treatment groups will be exposed on one occasion to the restraint stress protocol described above, while the final treatment group will represent an undisturbed control group. Because this is an acute stress challenge, the timing of implementation is extremely important. Oviposition will be monitored to determine the precise time of oviposition. After oviposition of a midsequence egg, ovulation of the next follicle will take place within approximately 30 min. This timing can be conveniently used to time stress protocols for the subsequent ovulations.

Restraint stress protocols will be conducted at two time points. One group of females (n=20) will be handled at approximately 16 h following the first oviposition (7 h prior to ovulation of the third egg), which should result in a CORT elevation approximately 2 h prior to meiotic segregation and 6 h prior to ovulation. For this experimental group, CORT levels early in the cycle are purposely altered, to allow time for genomic effects associated with CORT, which can take up to several hours (Lösel et al., 2003, *Physiology Reviews*; S3:965-1016) to take place. The second group of females will be handled at approximately 19 h following the first oviposition (5 h prior to ovulation of the third egg), which should result in a CORT elevation at meiotic segregation, 4 h prior to ovulation. This treatment will allow us to identify faster-acting effects (Lösel et al., 2003, *Physiology Reviews*; S3:965-1016) associated with CORT on developing oocytes. Both treatments and the segregation event take place prior to the natural CORT peak produced prior to lights on. After the stress period, females will be returned to their home cages and oviposition will be monitored rigorously through the nesting cycle, laying order will be marked, and eggs will be collected after 2 d of incubation for molecular sexing of embryos.

Experiment 3B

Effects of CORT Injection Prior to Ovulation on Offspring Sex

This experiment is designed to repeat Example 3 with an increased sample size, and also using two time points as in Expt. 3a. Hens will be randomly distributed to one of five treatment groups (n=40 in each): Two of the groups (n=20 each) will be exposed to a pharmacological dose of CORT (20 ug) dissolved in peanut oil, two will receive a physiologically high dose (1 ug, 15× lower than that used in Example 3, while the final treatment group will receive a control injection of vehicle (peanut oil) only. Timing of the experiment will be the same as that described and illustrated for experiment 3a to tease out rapid and longer-acting effects of CORT on processes that determine offspring sex in hens.

It is expected that, for the acute stress and CORT injection groups, a significantly higher proportion of males compared to females will be produced in the egg that is ovulated just after treatment, while control and control injection groups should have approximately equal numbers of males and females in the same egg. If this is, in fact, the case, it would be useful given more time and birds to add another treatment group to Expt. 3a that receives a silastic implant of metyrapone, which does not affect basal levels of CORT but inhibits the stress-induced increase in CORT. In this case, it is expected CORT to remain basal and sex ratios to remain unbiased.

Aside from the data and results of previous example, the following evidence supports the idea that CORT may act directly on the oocyte to skew offspring sex: (1) There are receptors for corticosterone throughout the avian ovary (Kucka et al., 2006, *General and Comparative Endocrinology;* 147:377-83). (2) Avian oocytes are exposed to CORT directly. In the bird, as ovarian follicles mature, they become richly innervated with growing blood vessels, allowing oocytes access to nutrients (including yolk precursors) and hormones such as CORT. In addition, the adrenal gland is embedded in the ovary, allowing for paracrine mediation as well. Finally, studies show that CORT acts directly on the avian oocyte to control ovulatory processes (Breuner et al., 2006, *Horm Metab Res;* 38:260-8). (3) There are mechanisms by which CORT can interact with the sex chromosomes within the oocyte. CORT interacts with proteins that are known to be involved with meiotic separation of sex chromosomes such as small ubiquitin-related modifier-1 (SUMO-1) and cyclin. Thus, the next step is to determine whether an acute exposure to a stressor and/or to elevated CORT levels prior to ovulation can alter the subsequently ovulated oocyte to skew offspring sex. The following experiment has been designed to address this hypothesis.

Experiment 4

Effects of CORT Exposure and Maternal Stress History on Sex Chromosome Segregation In Vitro For this experiment, the largest (F1) preovulatory follicles will be collected from female ovaries approximately 4 h prior to ovulation (prior to the completion of meiosis 1) and allow them to undergo the ovulation process in vitro in either control culture medium or in culture medium supplemented with a 20 ng/ml concentration of CORT, which simulates CORT concentrations in the upper physiological range circulating in female blood. Follicles undergo ovulation within 24 h of culture, after which ovulated oocytes will be fertilized in vitro by pipetting a small drop of semen collected and pooled from 10 roosters onto the germinal disc of the oocyte (see below for detailed protocols). This process of ovulation and fertilization in vitro was originally used in a quail model system and has since been validated for chickens, and this procedure has been used successfully in a chicken model system (Batellier et al., 2003, *British Poultry Science;* 44:819-20).

Females from which follicles are collected will be assigned to one of three treatment groups (n=80 per group): (1) a chronic stress treatment group (described in Expt. 1A above) which will experience perceived food limitation, (2) a CORT implant group (described in Expt. 1B above), and (3) a control group receiving no treatment and having ad libitum access to food both visually and physically. Follicles collected from these females will be cultured in either the control or media supplemented with 10 ng/ml CORT, a dose in the physiological range of circulation (n=30 per group) until ovulation, creating the six treatment groups.

After ovulation and fertilization, fertilized oocytes will be maintained in control culture medium and incubated for 4 d to allow for embryonic development, after which embryos will be separated and sexed using PCR-based molecular techniques. The purpose of developing embryos for 4 d because embryonic growth in culture is slower than natural growth and to ensure accurate sexing independent of maternal contamination. This full process (from ovulation through embryo development) has been shown to have an approximately 50% success rate. Thus initial sample sizes are large to account for potential oocyte loss.

If CORT exerts direct effects on the oocyte to distort chromosome segregation, then, based on preliminary experiments, it is expected that a statistical majority of oocyte ovulated in CORT supplemented media will produce male-biased embryos. If long-term and short-term CORT elevations act on sex ratios through different mechanisms, it is expected that follicles collected from chronically and CORT implanted females will produce predominantly females, regardless of culture treatment. If follicles from chronically stressed and control treatment females respond differently to acute CORT exposure in culture, expression of glucocorticoid receptors (GR) on follicles collected from females in similar treatment groups will be quantified in further experiments.

The proposed studies will elucidate whether CORT acts directly at the levels of the sex chromosomes or through a series of mediating factors, such as through follicular growth, or through other circulating hormones to skew offspring sex ratios.

Materials and Methods

Animal maintenance and breeding. Fertilized eggs of white leghorn Hyline 36 hens will be obtained from the breeder and will be maintained until reproductive maturity (approximately 17 wks of age) in floor pens according to breeder recommendations. At 17 wks of age, hens will be transferred to layer cages and will remain there throughout the duration of the study with ad libitum access to a specially formulated breeder diet and water.

PCR based molecular sexing analyses. Genomic DNA will be extracted from tissue using the DNeasy Blood and Tissue Kit from Qiagen. DNA concentration and quality will be assessed using a nanodrop spectrophotometer (Wilmington, Del. USA). To assess sex of embryos, PCR-based sexing analysis will be conducted according to methods described in Griffiths et al. (Griffiths, R et al., 1998, *Molecular Ecology;* 7:1071-5). Two primers amplifying a region of the CHD gene and validated in chickens by our group and others will be used: P8 (5'-CTCCCAAGGATGAGRAAYTG-3') (SEQ ID NO:1) and P2 (5'-TCTGCATCGCTAAATCCTTT-3') (SEQ ID NO:2). PCR amplification will be carried out in a total volume of 25 ml with final reaction conditions as follows: 50 mM KCl, 10 mM Tris-HCL PH=9, 1.5 nM $MgCl_2$, 0.1% Triton X-100, 200 uM each dNTP, 100 ng each primer and 0.15 units of Taq polymerase. PCR will be performed using a BIO-RAD thermocycler. An initial denaturing step at 94° C. for 1 min will be followed by 30 cycles of 48° C. for 452, 72° C. for 45 s, and 94° C. for 30 s, and finally a final fun of 48° C. for 1 min. Bands will be visualized on a 2.3% agarose gel stained with ethidium bromide. One band is indicative of a male while two bands is indicative of a female.

Blood sampling, yolk sampling, and hormone analyses. Blood samples will be collected from the brachial vein. Plasma will be isolated via centrifugation and frozen at −20° C. until hormone analyses. For yolk samples, one-half of the whole yolk will be homogenized and a 50 mg sample will be collected and stored at −20° C. in 500 ul $dH_2O$. To quantify steroid hormones (corticosterone, testosterone, and progesterone) in both plasma and yolk, hormones will be separated via liquid column chromatography and quantified using a standard competitive binding radioimmunoassay according to Schwabl (Schwabl, 1993, *PNAS;* 90:11446-50) and Mendonga et al. (Mendonga et al., 1996, *Hormones and Behavior;* 30:153-61). Leptin will be quantified in plasma using the remaining 20 ul of plasma with an ELISA using a polyclonal peptide antiserum that was developed for universal use and has been validated in chickens.

In vitro ovulation and fertilization. Following protocols successfully executed in both quail and chickens (Batellier et al., 2003, *British Poultry Science;* 44:819-20; Olszanska et al., 1996, *British Poultry Science;* 37:929-35; Olszanska et al., 2002, *Journal of Comparative Zoology Part A;* 292:580-6), F1 Follicles will be excised from females at 4 h prior to ovulation and will be hung in a glass receptacle containing Dulbecco Medium (DMEM) or DMEM plus a CORT supplement of 10 ng/ml medium. Follicles will be incubated at 41° C. until ovulation occurs, which is clearly visible when the oocyte drops to the bottom of the glass receptacle. After ovulation, 10 ul of a sperm suspension ($1$-$2\times10^6$ sperm/ml) will be placed on the germinal disc and incubated for 15-20 min at 41° C. The fertilized oocytes will then be washed of excess sperm and incubated in a mixture of control DMEM and chicken egg albumen (at a mix of 1:2 v:v) at 41° C. for 2 d (the earliest stage of development which can be used for PCR-based molecular sexing). Embryos will then be excised and analyzed using molecular sexing analysis.

Follicular growth rate and developmental period. Because the density of yolk lipids deposited are high during the day and low at night, distinct growth rings are created within the yolk. By measuring the width of and counting those rings, the growth rate and the total growth during the rapid yolk deposition phase of the follicle can be calculated. Each layer corresponds to approximately 12 h of yolk deposition (Hodges et al., 2002, *Human Reproduction;* 17:1171-80). Follicular growth rate and total growth will be measured and calculated according to Young and Badyaev (Hodges et al., 2002, *Human Reproduction;* 17:1171-80). Briefly, yolks will be frozen and a 2 mm slice will be cut from the center and slices will be incubated in 1.5 ml 4% formalin at 60° C. for 12 h. Yolk slices will then be rinsed and stained using 6% potassium dichromate, and incubated at 60° C. for another 12 h. After staining, yolk slices will be rinsed and cut in half to reveal yolk layers which will be photographed using a 10 megapixel digital camera and analyzed using SigmaScan software (SPSS Inc., Chicago, USA). Duration of development will be determined by counting and measuring light and dark lipid layers. Daily lipid acquisition will be used to calculate the duration and rate of oocyte development. To measure daily lipid acquisition, the distance from the centre of the yolk to the outer boundary of each layer pair (one light and one dark layer equaling 24 h of growth) will be measured. Measurements will be repeated three times at equally spaced rotations to each other and a mean was used in the analyses. These data will be analyzed using similar statistical methods described in Young and Badyaev (Young and Badyaev, 2004, *J Evolutionary Biol;* 17:1355-66).

Statistical analyses. For simple experimental designs, percentages of females that produce male offspring will be compared using chi square analyses. Based on recommendations by Wilson and Hardy (Wilson, K and Hardy, ICW. Statistical analysis of sex ratios: an introduction. In: Sex ratios: Concepts and Research Methods, Cambridge, UK: Cambridge University Press; 2002), all sex ratio data will be treated as grouped binary variables and arcsin transformed. When analyzing among treatment groups, a generalized linear model will be conducted. When comparing sex ratios with continuous variables such as hormone concentrations and follicular growth rates, untransformed data and logistic regressions will be used. Hormone data will checked for homogeneity of variance, and will be log-transformed when they are not normally distributed. Hormone concentrations among treatment groups will be analyzed using an Analysis of Variance (ANOVA). All statistical tests will be conducted using JMP.8 statistical software (SAS Inc, Cary, N.C., USA).

Example 7

Figure 8:
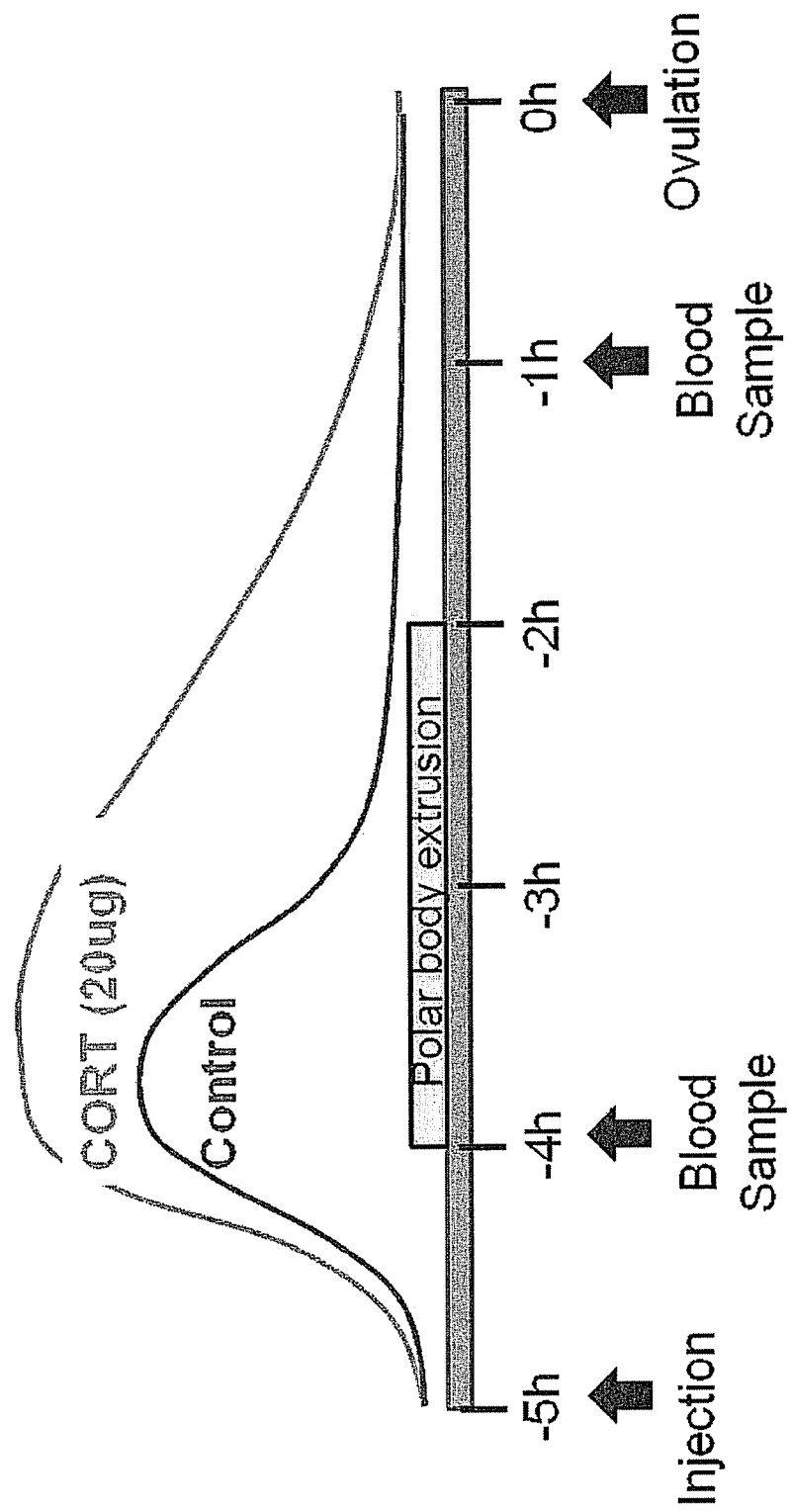
FIG. 8. With control injections, the acute stress of the injection occurred at five hours prior to ovulation. CORT concentrations rose significantly within twenty minutes, but declined again by four hours post-injection, while elevations resulting from administration of the pharmacological dose of CORT remained elevated for the entire four hour period during which meiotic segregation is likely occurring.

Effects of Dose and Timing of Corticosterone Administration on Offspring Sex Ratios In the previous examples, the acute stress of the control injection occurred at five hours prior to ovulation. CORT concentrations rose significantly within 20 minutes but declined again by four hours post-injection, while elevations resulting from administration of the pharmacological dose of CORT remained elevated for the entire 4 h period during which meiotic segregation likely happened (FIG. 8). As a result, two factors differed between the control and the CORT treated groups. One, the level to which circulating CORT was elevated and, two, the time during which CORT was elevated. Examples 7 and 8 will determine whether a lower dose of CORT (more physiological in nature) can stimulate a male-bias in the sex ratio and whether CORT is truly the mediator responsible.

Experiment A

Figure 9:
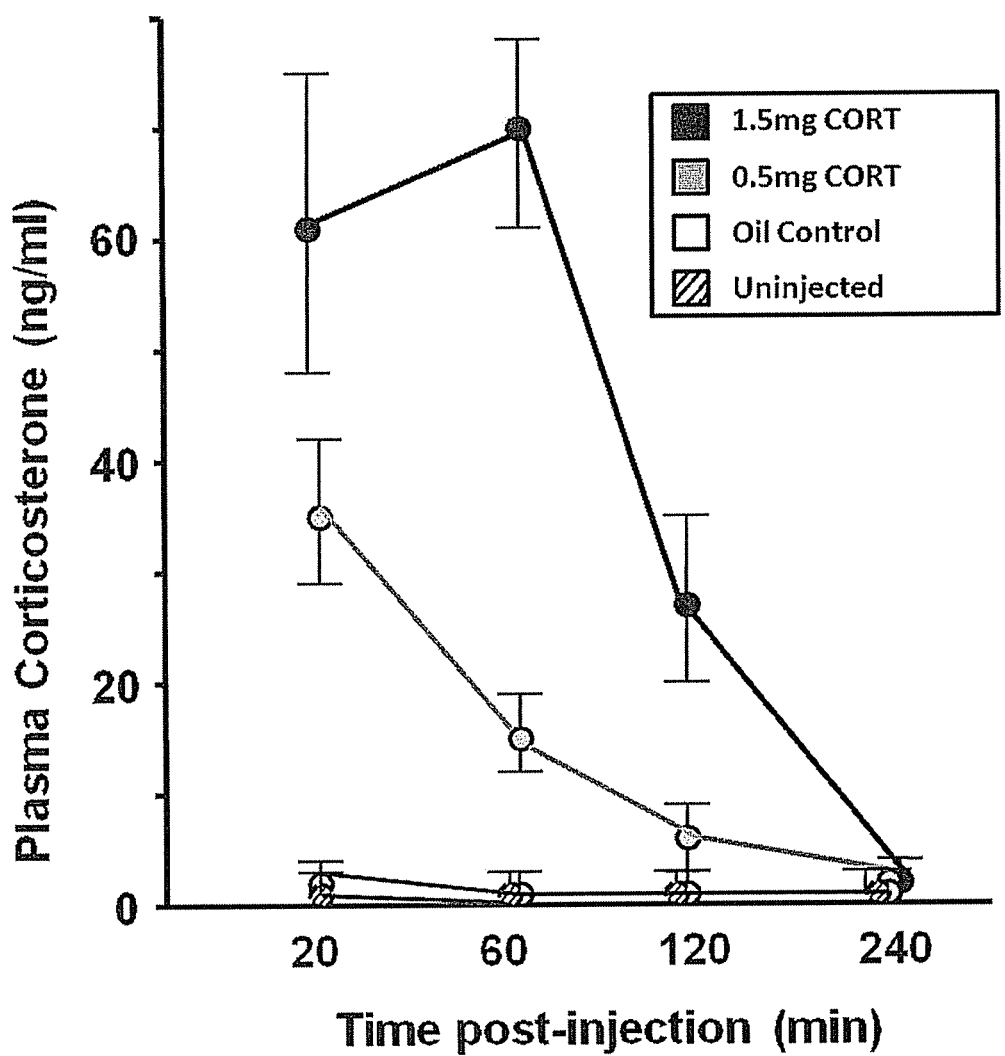
FIG. 9. Plasma corticosterone concentrations in hens after injections of 1.5 mg CORT, 0.5 mg CORT, oil control, and uninjected.

Effects of Acute Physiological and Pharmacological CORT Exposure in the Presence and Absence of a CORT Antagonist In Vivo To test for a dose-dependent effect of CORT on sex ratios, female leghorns will be housed in layer cages, provided access to food and water ad libitum and will be randomly divided into one of seven treatment groups (n=72 each). Two of the groups will receive a pharmacological dose of CORT (1.5 mg) dissolved in peanut oil, two will receive a physiologically high dose (0.5 mg), which has been shown to elevates CORT concentrations to just below 40 ng/ml, which is within the physiological range (FIG. 9), and two will receive a control injection of vehicle (peanut oil) only. To test whether CORT is a mediator in the sex determination process, one group from each of these treatment sets will also receive a dose of RU-486 (0.5 mg dissolved in 500 ul dH20), a glucocorticoid receptor blocker, administered 15 min prior to the injection treatment itself. While RU-486 plays a dual role, acting as a progesterone receptor antagonist, in mammals, the chicken progesterone receptor does not bind to RU-486 due to a single amino acid substitution. As a result, treatment with RU-486 should not interrupt normal laying cycles. One final group will receive no injection treatment.

Injections will take place 5 h prior to ovulation (as above) which produces a CORT peak prior to the natural CORT peak that occurs just prior to lights on. After the injections, females will be returned to their home cages and subsequently ovulated eggs will be collected the following day. Sexes of eggs will be compared among treatment groups using molecular sexing analyses. In addition to sex ratios, yolk will be collected from all eggs to determine yolk CORT and testosterone concentrations. Blood will also be sampled from a subset of females (n=12) (from which sex ratios will not be collected), to measure CORT and other potential hormones involved in the process (such as testosterone) as well. This experiment will test whether a pharmacological dose of CORT is necessary to skew sex ratios and whether CORT is truly an involved mediator.

It is expected that the pharmacological dose of CORT will induce a male-biased sex ratio. If a physiological dose is sufficient to alter sex ratios, a male bias will be seen in the low-dose group as well. If a biased sex ratio is not seen in the physiological treatment group, it may be that the dose is insufficient to induce either the direct or indirect effects necessary, or that pharmacological and physiological doses are acting through different receptors.

If the pharmacological and/or physiological doses of CORT stimulate and effect sex ratio as a result of GR activation, treatment with RU-486 should block this effect. If RU-486 does not block this effect, then the effect may instead occur through activation of MRs. If RU-486 does not inhibit CORT induced sex ratio skews, an additional group of birds treated with fludrocortisone (0.3 mg in 50 ul peanut oil), which is an MR agonist for which GRs have a very low affinity, will be added.

Given that the act of a control injection itself produces a corticosterone increase, a male bias may be observed in the control treatment group. This was not the case in Example 3, however sample sizes were low in the control group. For this reason, an un-injected control group has been added for additional comparison.

If the physiological dose of CORT does not induce an effect on the sex ratio, it is possible that, rather than being too low, this dose is metabolized too quickly and does not affect the follicle at exactly the right time. Expt B, below, will address this possibility.

Experiment B

Effects of Timing of CORT Exposure on Offspring Sex Ratios Using Several Doses

Figure 10:
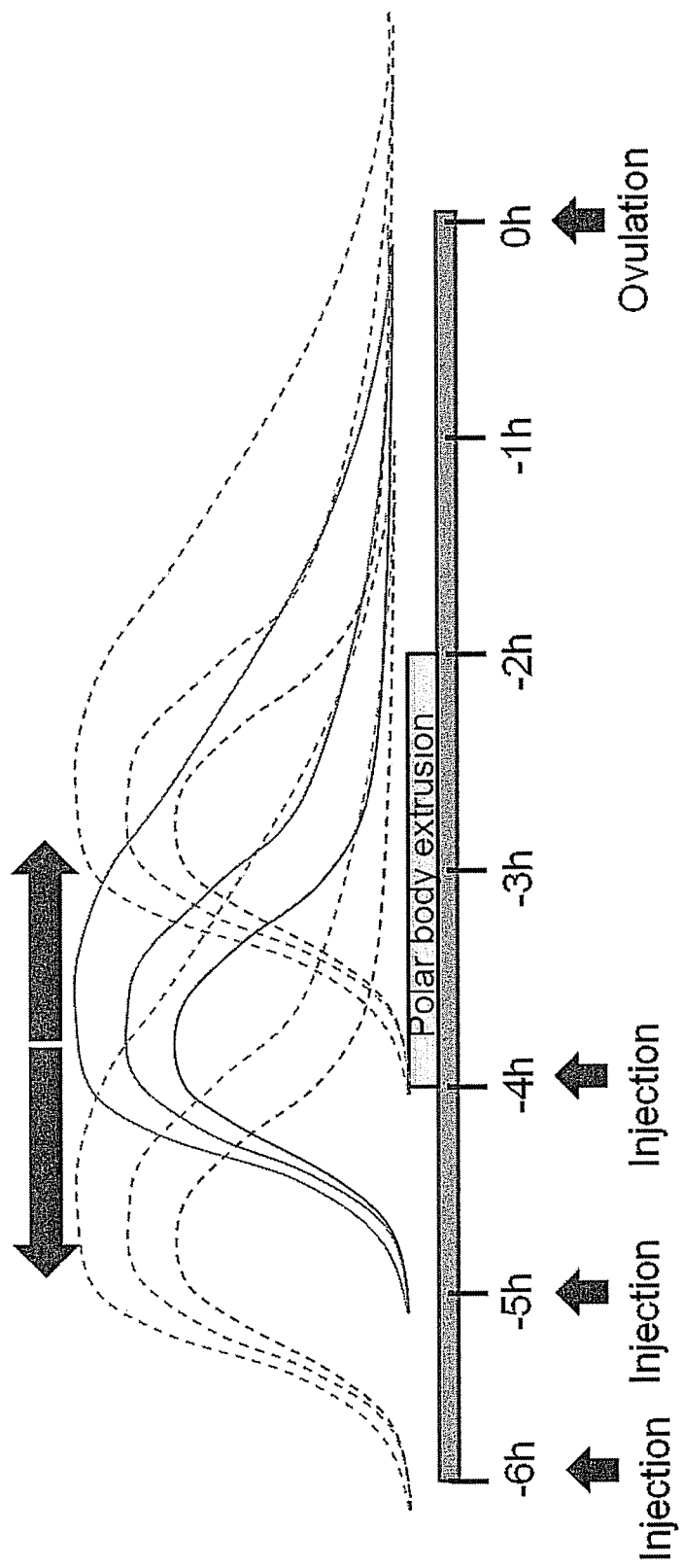
FIG. 10. Timeline for CORT injection of white leghorn hens at four, five, and six hours prior to ovulation.

It is possible that the timing of the CORT peak relative to the meiotic segregation event may alter the magnitude of the effects of CORT on sex ratios (or potentially even the direction in which the sex ratios are skewed). Experiment B will test this using white leghorn hens housed as described above. Hens will be randomly allocated into one of eight treatment groups (n=80 each). Two of the groups will receive a pharmacological injection of CORT (1.5 mg) as above, two will receive a physiological dose (0.5 mg) as above, two will receive a control injection of peanut oil only, and the final two will receive no injection. Half of the hens will then be divided into one of two injection times −6 h prior to ovulation and 4 h prior to ovulation. Eggs will be collected and analyzed in a similar manner to Experiment A, above. Results from these time points will be compared with results from Experiment A, where injections are conducted at 5 h prior to ovulation as in preliminary experiments. This will allow us to analyze the effects of several levels of CORT at several different precise times during meiotic segregation. Blood samples will be taken 1 and 2 h after each injection from a subset of hens (n=20) to ensure the expected level of the CORT peak. This is represented schematically in FIG. 10.

Example 8

Test for Direct Effects of CORT on Ovarian Follicles to Alter Sex Ratios

Aside from the preliminary data and results of studies already discussed, other data support the idea that CORT may act directly on the oocyte to skew offspring sex. There are glucocorticoid receptors on the avian germinal disc and enzymes that break down corticosterone throughout the avian ovary. Studies have shown that CORT acts directly on the avian oocyte to control ovulatory processes and avian oocytes are exposed to CORT directly (as ovarian follicles mature, they become richly innervated with growing blood vessels, allowing oocytes access to nutrients (including yolk precursors) and hormones such as CORT). Experiments A and B, described in more detail below, will test whether direct stimulation of follicles with CORT in vitro will cause a sex ratio skew (Experiment A) and whether there are receptors available on the preovulatory follicle to respond to CORT (Experiment B).

Experiment A

Exposure of Periovulatory Oocytes to CORT and a CORT Antagonist In Vitro

For this experiment, the largest (F1) preovulatory follicles will be collected from female ovaries approximately 5 h prior to ovulation (prior to the completion of meiosis 1) and allowed to undergo the ovulation process in vitro in one of three conditions (n=140 per group): control culture medium containing no hormone, culture medium supplemented with a 50 ng/ml concentration of CORT, which simulates CORT concentrations in the upper physiological range circulating in female blood, or culture medium supplemented with 50 ng/ml CORT and 64 umol/L RU-486 (dose based on prior granulosa cell culture experiments), a GR antagonist. If Example 7, Experiment A indicates that a pharmacological dose is necessary to stimulate sex ratio skews, the dose used here will be adjusted as necessary, and if Example 7, Experiment B indicates that different timing is more effective, this will also be adjusted. Follicles undergo ovulation within 24 h of culture, after which oocytes will be frozen, sectioned, and sex assessed using in situ hybridization.

Experiment B

Documentation of Receptor Location and Dynamics in Ovarian Tissue Surrounding the Time Point of Meiotic Segregation F1 follicles will be collected from untreated females at three time points in the period before ovulation (5, 3, and 1 hour before ovulation; n=10/time period). Follicles will be immediately placed in ice cold Krebs buffer and follicle layers (theca, granulosa, and germinal disc) will be dissected under a high power binocular scope. Half of each tissue will be stored in RNAlater to preserve RNA for extraction. GR, MR, and AR expression will be quantified on each layer using quantitative real-time PCR. The other half of each tissue will be immediately frozen at −80° C. to quantify presence of GR, MR, and AR using Western Blot analyses. This assessment will determine whether follicles and, in particular, the oocyte, are capable of responding directly to glucocorticoids and where in the follicles these effects may be taking place during the critical time period surrounding meiotic segregation.

If CORT acts directly at the level of the ovarian follicle, it is expected that significantly more follicles will retain the Z sex chromosome when incubated with CORT compared with control media. If this effect occurs through GRs on the follicle, RU-486 should block this effect.

If an effect of CORT is not seen on sex ratios, it cannot be definitively conclude that CORT does not act at this level. It is possible that another hormone or factor not present in the culture system plays a conjunctive role. However our measurement of GR, MR, and AR will provide insight into the capability of the various follicular portions to respond to glucorticoids and testosterone. If CORT acts on sex ratios through these receptors, they should be present in the GDR and change over time.

Example 9

Effects of Chronic CORT Elevation on Offspring Sex Ratios

Previous experiments in other species have consistently shown that chronic elevations of CORT stimulate a female-biased sex ratio. While the present examples in chickens show that short-term treatment of hens with CORT at meiotic segregation stimulate a male biased sex ratio, it is possible that chronic elevations act via a different mechanism entirely. For example, chronic (i.e. over days or weeks) CORT elevation may act on sex ratios by affecting follicular dynamics that in turn influence offspring sex. In chickens, exogenous CORT treatment through implants reduces the amount of yolk precursors available for growth during the rapid yolk deposition phase. Perhaps CORT acts to depress the follicular growth rate during the week-long process of rapid yolk deposition, which itself has been shown to skew offspring sex ratios. Alternatively, chronically elevated CORT may act to influence other hormones and factors that subsequently influence offspring sex. Of course, it is also possible that chronic CORT elevations down-regulate CORT receptors on the oocyte that would normally trigger a male-bias, or that our acute pharmacological dose of CORT exerted different effects than would a dose in the physiological range. As a result, it is necessary to establish whether chronic elevations of CORT produce a female-biased sex ratio in this species, and, along the way, assessments cannot be made that would lend insight into how chronic CORT may affect sex ratios, if it exerts an effect.

White leghorn hens will be singly housed (except during the chronic stress group described below) in cages with access to food and water ad libitum. Hens will be randomly divided into 4 groups (n=90 each): The first group will receive an implanted Azet osmotic pump which delivers CORT at a rate of 5.0 ul/hr (0.3 mg CORT dissolved in PEG-400/hr) for two weeks. The second will receive a pump containing only the solvent (PEG-400). The third will be exposed to a social stress protocol, during which hens are pair-housed, and partners are rotated once daily to ensure a new neighbor each time. Hens will never be paired with the same hen twice throughout the course of the 2 week rotation period. This protocol has routinely been used in chickens as a method of long-term stress, and induces elevations in CORT concentrations to around 11 ng/ml. Daily movement of hens will prevent acclimation and should ensure elevation of CORT throughout the chronic stress period. A final group of hens will receive no treatment. Hens will be artificially inseminated twice weekly throughout the treatment period and eggs will be collected and marked each day. Eggs will be incubated for 7 d and embryos will be collected and sexed using molecular techniques. Specific comparisons will be made between sexes of eggs collected at the beginning of the experiment and eggs collected at 1 and 2 weeks into the stress protocol. Finally, sexes of eggs collected 1 and 2 weeks after CORT concentrations return to basal levels will also be assessed to determine how long the chronic stress continues to exert effects after CORT concentrations have decreased. Blood samples will be collected from subsets of hens (n=10) twice weekly to determine CORT concentrations throughout the experiment.

In addition to sex ratios, additional information will be collected. Eggs will be collected from a subset of hens (n=15) within each treatment group at each time point and will assess follicular growth rates (see detailed methods below) and a subset of hens (n=15) will be euthanized at the time of meiotic segregation, collect the largest (F1) follicle and assess the presence and quantity of GRs and MRs on those follicles using qPCR.

If chronic CORT acts in a similar manner in chickens as it does in other species, a female-biased sex ratio will be seen in both the CORT implanted group as well as in the socially stressed group. If, on the other hand, CORT elevations act in a different manner in chickens and the elevation of CORT at the time of meiotic segregation is truly exerting the effect as it did during our acute treatments, a male-biased sex ratio. If CORT exerts an effect on sex ratios via changes in follicular growth (as has been documented in other avian species), follicular growth rates should be lower in the stressed and CORT-treated groups. If CORT exerts an effect via a down regulation of receptors that respond to CORT, lower expression of GRs and/or MRs on the F1 follicles collected from stressed and CORT-treated hens will be seen.

Example 10

Effects of CORT on Sex Ratios in Other Chicken Strains

For the previous examples, white leghorn are used because leghorn hens lay very reliably and it is easy to time ovulation and oviposition. However, it is also important to test for similar effects in other strains. This example will test for the same effects of acute (and potentially chronic) CORT in broiler breeders. This example will determine the effects of acute and chronic treatment with CORT on sex ratios in broiler breeders. Broiler breeders will be housed singly in cages with access to water ad libitum but will be placed on a skip-a-day feeding regimen up until the point that they are reproductively mature. This regimen has been shown to prevent excessive fat accumulation while also reducing the psychological stress associated with daily feeding of smaller amounts of food. Once reproductively mature, hens will be fed restricted amounts of food once daily, as is general practice for these birds. Hens will be randomly divided into one of four treatment groups (n=60). The first group will receive an acute injection of the optimal dose of CORT determined in Example 7, Experiment A, at the optimal injection time determined in Example 7, Experiment B for leghorn hens. The second group will receive a control injection at the same time point. The third group will receive an osmotic pump containing CORT (as in Example 9) and the fourth will receive an implant containing only PEG-400. Chronic CORT elevations will be maintained using these pumps for 2 weeks and eggs will be sampled in a similar manner to Example 7, Experiments A and B (for acute treatments) and Example 9 (for chronic treatments).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Sequence Listing Free Text

SEQ ID NO:1-2 Synthetic oligonucleotide primers

```
SEQUENCE LISTING

<160> NUMBER OF SEQ ID NOS: 2

<210> SEQ ID NO 1
<211> LENGTH: 20
<212> TYPE: DNA
<213> ORGANISM: artificial
<220> FEATURE:
<223> OTHER INFORMATION: synthetic oligonucleotide primer

<400> SEQUENCE: 1
ctcccaagga tgagraaytg                                            20

<210> SEQ ID NO 2
<211> LENGTH: 20
<212> TYPE: DNA
<213> ORGANISM: artificial
<220> FEATURE:
<223> OTHER INFORMATION: primer
```

```
<400> SEQUENCE: 2
tctgcatcgc taaatcctتt                                           20
```

What is claimed is:

1. A method of altering the sex ratio in avian offspring, the method comprising the acute administration of an adrenal glucocorticosteroid to an ovulating avian female.

2. A method of influencing the sex chromosome ovulated by a female bird, the method comprising the acute administration of an adrenal glucocorticosteroid to an ovulating female bird.

3. The method of claim 1, wherein the adrenal glucocorticosteroid is corticosterone.

4. The method of claim 1, wherein the glucocorticosteroid is provided before the completion of meiosis I in an oocyte and/or at the time of sex chromosome segregation in an oocyte.

5. The method of claim 1, wherein the glucocorticosteroid is provided after the completion of rapid yolk deposition and prior to ovulation.

6. A method of altering the sex ratio in avian offspring, the method comprising providing an adrenal glucocorticosteroid to an ovulating avian female by exposing the ovulating avian female to a stress.

7. The method of claim 1, wherein the resultant sex ratio in the avian offspring is more than 50% male offspring.

8. The method of claim 1, wherein the probability of a male embryo is greater than 50%.

9. A method of influencing the sex chromosome ovulated by a female bird or altering the sex ratio in avian offspring, the method comprising the administration of an inhibitor of a stress hormone.

10. The method of claim 9, wherein the inhibitor of a stress hormone is administered before the completion of meiosis I in an oocyte, at the time of sex chromosome segregation in an oocyte, or provided after the completion of rapid yolk deposition and prior to ovulation.

11. The method of claim 9, wherein the resultant sex ratio in the avian offspring is more than 50% male offspring or more than 50% female offspring.

12. The method of claim 1, wherein the avian is a chicken.

13. The method of claim 12 wherein the chicken is a broiler or a layer.

14. The method of claim 1, wherein the avian is a passerine or an exotic.

15. The method of claim 1, wherein acute administration of the adrenal glucocorticosteroid consists of administration in the interval of the completion of rapid yolk deposition to ovulation.

16. The method of claim 1, wherein acute administration of the adrenal glucocorticosteroid comprises administration of a single dose of an adrenal glucocorticosteroid.

17. The method of claim 1, wherein acute administration of the adrenal glucocorticosteroid consists of administration about one to about six hours prior to ovulation.

18. The method of claim 1, wherein acute administration consists of administration just prior to the completion of Meiosis I and sex chromosome segregation.

19. The method of claim 1, wherein administration is oral or topical administration.

20. The method of claim 1, wherein administration is by injection.

* * * * *